(12) United States Patent
Fischer et al.

(10) Patent No.: US 11,221,373 B2
(45) Date of Patent: Jan. 11, 2022

(54) METHOD AND DEVICE FOR DETECTING EARLY BATTERY DEPLETION CONDITION

(71) Applicant: PACESETTER, INC., Sylmar, CA (US)

(72) Inventors: Avi Fischer, Los Angeles, CA (US); Gene A. Bornzin, Simi Valley, CA (US); Thomas F. Strange, Easley, SC (US); Xing Pei, Thousand Oaks, CA (US); Aditya Goil, Stevenson Ranch, CA (US); Fady Dawoud, Santa Clarita, CA (US); Kyungmoo Ryu, Palmdale, CA (US); Joseph Beauvais, Liberty, SC (US); Gabriel Mouchawar, Valencia, CA (US); Richard Williamson, Santa Monica, CA (US)

(73) Assignee: PACESETTER, INC., Sylmar, CA (US)

( * ) Notice: Subject to any disclaimer, the term of this patent is extended or adjusted under 35 U.S.C. 154(b) by 1072 days.

(21) Appl. No.: 15/631,184

(22) Filed: Jun. 23, 2017

(65) Prior Publication Data

US 2018/0372805 A1    Dec. 27, 2018

(51) Int. Cl.
*G01R 31/392* (2019.01)
*G01R 31/36* (2020.01)
(Continued)

(52) U.S. Cl.
CPC ......... *G01R 31/392* (2019.01); *A61N 1/3708* (2013.01); *G01R 31/367* (2019.01); *G01R 31/3648* (2013.01); *G01R 31/3835* (2019.01); *G01R 31/396* (2019.01); *H01M 10/4285* (2013.01); *H01M 10/48* (2013.01); *H02J 7/0047* (2013.01); *A61N 1/3956* (2013.01); *H01M 2220/30* (2013.01); *H02J 7/0048* (2020.01); *H02J 7/0063* (2013.01)

(58) Field of Classification Search
CPC ............ G01R 31/3679; G01R 31/3658; G01R 31/3651; H02J 7/0047
See application file for complete search history.

(56) References Cited

U.S. PATENT DOCUMENTS 5,411,537 A * 5/1995 Munshi ................ A61N 1/3708
320/163
5,620,474 A * 4/1997 Koopman ............ A61N 1/3708
607/29

(Continued)

OTHER PUBLICATIONS

Extended European Search Report—EP App No. 18178934.8—EP Counterpart Application.

*Primary Examiner* — Manuel A Rivera Vargas
*Assistant Examiner* — Yaritza H Perez Bermudez
(74) *Attorney, Agent, or Firm* — The Small Patent Law Group LLC; Dean D. Small

(57) ABSTRACT

Methods, devices and program products are provided for determining an early battery depletion condition for a battery powered device. The method determines a charge consumption drawn externally from a battery cell by the device for a select period of time, obtains a measured cell voltage for the battery cell of the medical device, calculates a projected cell voltage based on the charge consumption and usage conditions, and declares an early depletion condition based on a relation between the measured and projected cell voltages.

31 Claims, 10 Drawing Sheets

(51) Int. Cl.
  *A61N 1/37*      (2006.01)
  *G01R 31/396*    (2019.01)
  *G01R 31/3835*   (2019.01)
  *G01R 31/367*    (2019.01)
  *H01M 10/42*     (2006.01)
  *H01M 10/48*     (2006.01)
  *H02J 7/00*      (2006.01)
  *A61N 1/39*      (2006.01)

(56) References Cited

U.S. PATENT DOCUMENTS

| | | | | |
|---|---|---|---|---|
| 5,684,404 A * | 11/1997 | Millar | G01R 31/3648 |
| | | | 324/426 |
| 5,736,835 A * | 4/1998 | Nakajo | H01M 10/48 |
| | | | 320/112 |
| 6,167,309 A * | 12/2000 | Lyden | A61N 1/378 |
| | | | 607/29 |
| 6,268,710 B1 * | 7/2001 | Koga | H02J 7/0021 |
| | | | 320/116 |
| 6,317,634 B1 * | 11/2001 | Lyden | A61N 1/025 |
| | | | 607/29 |
| 8,942,935 B2 * | 1/2015 | Michaels | G01R 31/382 |
| | | | 702/63 |
| 2002/0171429 A1 * | 11/2002 | Ochiai | G01R 31/374 |
| | | | 324/426 |
| 2003/0160588 A1 * | 8/2003 | Kroll | H02J 9/061 |
| | | | 320/103 |
| 2004/0039424 A1 * | 2/2004 | Merritt | A61N 1/3708 |
| | | | 607/29 |
| 2007/0179547 A1 * | 8/2007 | Armstrong | A61N 1/3708 |
| | | | 607/29 |
| 2009/0182517 A1 * | 7/2009 | Gandhi | A61B 5/0084 |
| | | | 702/58 |
| 2014/0242420 A1 * | 8/2014 | Schaffner | H01M 10/48 |
| | | | 429/9 |
| 2014/0253039 A1 * | 9/2014 | Barsukov | H02J 7/007184 |
| | | | 320/112 |
| 2015/0349385 A1 * | 12/2015 | Hu | H01M 10/48 |
| | | | 429/91 |
| 2017/0003356 A1 * | 1/2017 | Kaib | G01R 31/389 |
| 2018/0143257 A1 * | 5/2018 | Garcia | G01R 31/382 |

* cited by examiner

METHOD AND DEVICE FOR DETECTING EARLY BATTERY DEPLETION CONDITION

BACKGROUND

Embodiments of the present disclosure generally relate to methods and devices to detect an early depletion condition in a battery powered device.

A variety of implantable and external portable electronic medical devices are utilized today in connection with a wide array of health related topics. Implantable and external portable medical devices utilize various types of battery-based power supplies, which ultimately need to be replaced or recharged. It is important to track the timing for replacement or recharge of the power supply in order to avoid loss of power by the medical device. Certain types of medical devices exhibit a certain amount of lead time, before the battery reaches an end of life (EOI) condition, in order to afford sufficient time to prepare for and implement replacement or recharge.

In certain instances, batteries have exhibited premature failure for various reasons. Although premature battery failure is an uncommon event in implantable medical devices, it does occur. Battery failure may have various implications, such as in pacemaker dependent patients, in patients utilizing cardiac resynchronization devices and in patients utilizing an implantable defibrillator.

By way of example, one mechanism of battery failure is the formation of lithium metal clusters that bridge between the cell cathode and anode/case electrode. The formation of lithium metal clusters may occur in both Lithium/Silver Vanadium Oxide and combination lithium/silver vanadium oxide & carbon monofluoride high rate battery cells. The lithium metal clusters form a low impedance pathway (similar to an internal short) for current to flow between the anode and cathode electrodes. The internal short has the same effect as an external load and thus prematurely depletes the battery cell. Another lithium metal clusters form a higher impedance pathway (similar to a high current load) for current to flow between the anode and cathode electrodes. Another mechanism for battery depletion is "poke through", which occurs as the cell ages, the cathode swells and the anode shrinks resulting in a short circuit between the anode and cathode electrodes.

SUMMARY

In accordance with embodiments herein a method is provided to determine an early battery depletion condition for a battery powered device. The method determines a charge consumption drawn externally from a battery cell by the device for a select period of time, obtains a measured cell voltage for the battery cell of the medical device, calculates a projected cell voltage based on the charge consumption and declares an early depletion condition based on a relation between the measured and projected cell voltages.

Optionally, the declaring operation may comprise identifying a divergence characteristic, between the measured and projected cell voltages, that is indicative of internal battery cell self-discharge. The method may declare a no early depletion condition when the measured and projected cell voltages fall with a tolerance range of one another. The method may obtain a steady state charge consumption and a task related charge consumption from the battery cell for the select period of time. The steady state and task related charge consumptions may be include within the charge consumption.

Optionally, the method may farther comprise recalibrating at least one of the projected cell voltage or charge consumption based on the measured cell voltage when a select criteria is maintained for a predetermined period of time. The recalibration operation may occur when the predetermined period of time passes without a capacitor discharge task occurring. The calculation operation may include utilizing at least one of a i) a voltage versus capacity curve associated with the battery cell; ii) a predetermined functional relation between voltage and charge capacity, or iii) an initial cell voltage, a cell voltage rate of change and the charge consumption for the period of time.

Optionally, the estimating operation may comprise obtaining an average charge consumption drained from the battery cell, and may estimate the charge consumption based on the average charge consumption over a period of time. During a transient recovery interval following a capacitor discharge task, the method may calculate a projected transient voltage and may utilize the projected transient voltage to calculate the projected cell voltage. The obtaining operation may include obtaining a plurality of the measured cell voltages and based thereon, may determine current and past measured rates of change. The past measured rate of change may correspond to a past period of time. The current measured rate of change may correspond to a current period of time. The declaring operation may include comparing the current and past measured rates of change to determine whether a difference there between exceeds a predetermined factor.

In accordance with embodiments herein a system is provided to determine an early battery depletion condition for a battery powered medical device. The system comprises a processor and memory storing program instructions accessible by the processor. Responsive to execution of the program instructions, the processor determines a charge consumption drawn externally from a battery cell by a medical device for a select period of time, obtains a measured cell voltage for the battery cell of the medical device, calculates a projected cell voltage based on the charge consumption and declares an early depletion condition based on a relation between the measured and projected cell voltages.

Optionally, the system may further comprise a housing for the medical device that includes the processor and memory such that the processor of the medical device declares the early depletion condition. The system may further comprise an external device that may communicate with the medical device. The medical device may include a measuring circuit to measure the cell voltage. The medical device may also include a transmitter to transmit the measured cell voltage to the external device. The external device may include the memory and processor to perform the estimating, obtaining, calculating and declaring operations. The system may further comprise an external device to communicate with the medical device. The medical device and the external device may include first and second processors, respectively, to share the estimating, obtaining, calculating and declaring operations.

Optionally, the processor may be configured to declare a no early depletion condition when the measured and projected cell voltages fall with a tolerance range of one another. The processor may be configured to declare recalibrate at least one of the projected cell voltage or charge consumption based on the measured cell voltage when a select criteria is maintained for a predetermined period of time The calculation operation may include utilizing at least one of a i) a voltage versus capacity curve associated with the battery cell; ii) a predetermined functional relation between voltage and charge capacity, or iii) an initial cell voltage, a cell voltage rate of change and the charge consumption for the period of time. The estimating operation may comprise obtaining an average charge consumption drained from the battery cell, and may estimate the charge consumption based on the average charge consumption over a period of time.

Optionally, the processor may be configured to, during a transient recovery interval following a capacitor discharge task, calculate a projected transient voltage and utilizing the projected transient voltage to calculate the projected cell voltage. The obtaining operation may include obtaining a plurality of the measured cell voltages and based thereon, may determine current and past measured rates of change. The past measured rate of change may correspond to a past period of time. The current measured rate of change may correspond to a current period of time. The declaring operation may include comparing the current and past measured rates of change to determine whether a difference there between exceeds a predetermined factor.

In accordance with embodiments herein, a method is provided to determine an early battery depletion condition for a battery powered device. The method comprises obtaining a plurality of the measured cell voltages; analyzing the plurality of measured cell voltages to identify a measured rate of change; comparing the measured rate of change with a rate of change threshold; and declaring an early depletion condition based on a relation between the measured rate of change and the rate of change threshold.

Optionally, the method further comprises determining current and past measured rates of change, wherein the past measured rate of change corresponds to a past period of time, the current measured rate of change corresponding to a current period of time, the rate of change threshold corresponding to a factor of the past measured rate of change. Optionally, the rate of change threshold includes a set of rate of change thresholds for different conditions, the conditions including at least one of: i) light current usage condition, ii) heavy current usage condition, iii) an early in battery life condition, iv) a late in battery life condition, or v) a day to day current drain level condition. Optionally, the measured rate of change represents a difference between two successive measured cell voltages divided by a time interval between cell voltage measurements.

In accordance with embodiments herein, a system is provided to determine an early battery depletion condition for a battery powered medical device. The system comprises a processor and memory storing program instructions accessible by the processor. Responsive to execution of the program instructions, the processor: obtains a plurality of the measured cell voltages; analyzes the plurality of measured cell voltages to identify a measured rate of change, compares the measured rate of change with a rate of change threshold, and declares an early depletion condition based on a relation between the measured rate of change and the rate of change threshold.

Optionally, the processor is further configured to determine current and past measured rates of change, wherein the past measured rate of change corresponds to a past period of time, the current measured rate of change corresponding to a current period of time, the rate of change threshold corresponding to a factor of the past measured rate of change.

DETAILED DESCRIPTION

Figure 1:
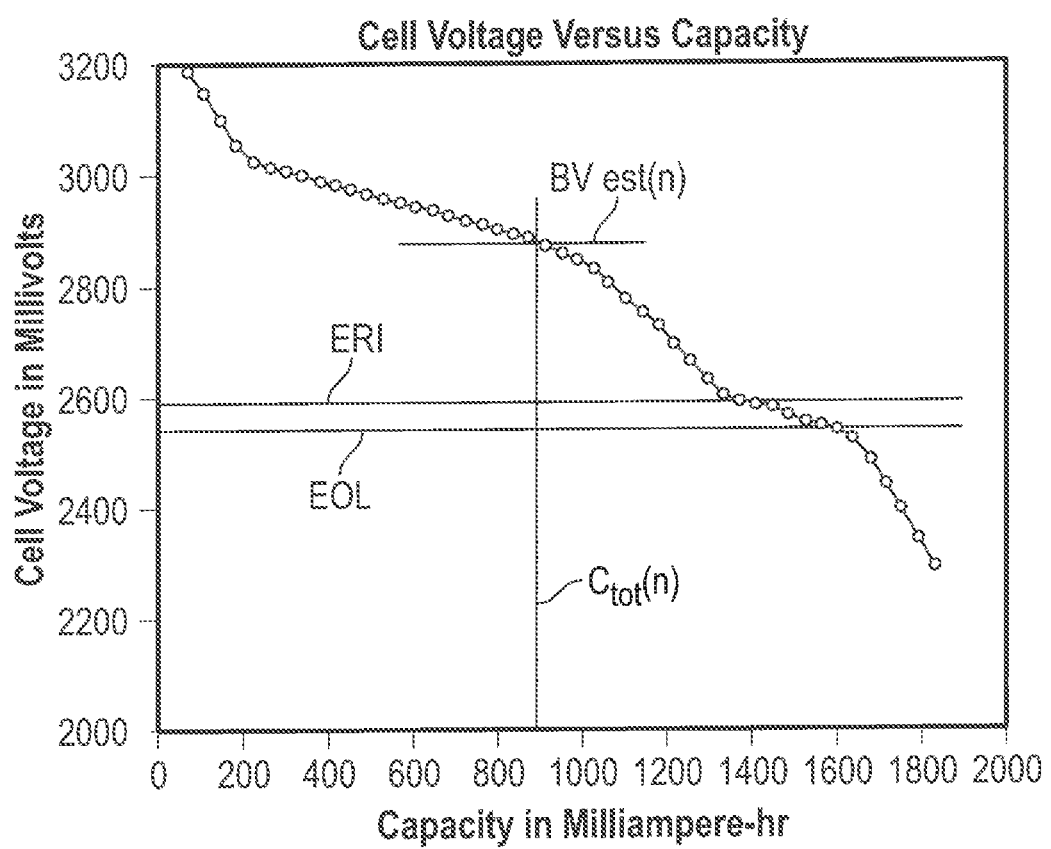
FIG. 1 illustrates a predictable cell voltage versus capacity profile for a model battery cell, such as a high quality cell made with chemically pure, predictable constituents in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Definitions

The term "task" refers to predefined operations to be performed by a medical device over a useful life of the medical device. The predefined operations may be in connection with delivering therapy, monitoring signals, communicating with other devices, self-diagnostics, internal maintenance and the like. Nonlimiting examples of device related tasks include reforming capacitors, delivering shocks or other therapy, performing telemetry operations, transmitting and receiving RF communications, performing expected self-discharge (about 1% per year) and the like.

The terms "estimated cell voltage" and "projected cell voltage", as used herein, refer to a voltage that may be derived from a predetermined model, formula or other pre-existing information. For example, projected cell voltages indicated in a model shown in FIG. 1 in connection with various amounts of capacity that are consumed from a model battery cell.

The terms "high drain" and "heavy current usage", as used in connection with describing various tasks performed by medical device, refer to tasks that draw at least a predetermined amount of charge, current or voltage from the cell, over time or per unit time. For example, high drain or heavy current usage tasks may be itemized by task name or task type (e.g., a capacitor charging task, capacitor reforming task, high-power communications task and the like). As another example, a high drain or heavy current usage task may represent a task that causes the battery cell to experience a transient voltage drop that does not fully recover from a some period of time (e.g., a few days).

The terms "low drain" and "low current usage", as used in connection with describing operation of the medical device, refer to all operations that are not high drain or heavy current usage tasks. For example, low drain or low current usage operations may be itemized by task name or task type (e.g., pacing, providing power to the microprocessors, A/D conversion, recording cardiac signals in memory). As another example, a low drain or low current usage operation represents continuous operations, during which the battery cell does not experience transient voltage drops.

The terms "battery", "battery cell" and "cell" are used interchangeably to refer to a single cell as well as more than one cell connected in parallel or series to form a common power supply. The cell(s) may be rechargeable or primary cells that are designed to be used once and then discarded. Non-limiting examples of the types of cells include Lithium/Silver Vanadium Oxide, a combination lithium/silver vanadium oxide & carbon monofluoride, and the like.

The following variables, as used throughout the present application, shall have the following means:

$I_{ss}(t)$=Steady state current drawn externally from a battery cell by a device such as when performing low drain or low current usage operations. The steady state current draw may be measured in real-time during operation of the device or may be represent a set or programmed value that is predetermined from tests, calculations or otherwise.

$I_{char}$=Current drawn externally from a battery cell by a device for a high drain charging task to charge a shock therapy storage circuit (e.g., capacitor). The current draw may be measured in real-time during operation of the device or may be represent a set or programmed value that is predetermined from tests, calculations or otherwise.

$I_{tele}$=Current drawn externally from a battery cell by the device during a high drain telemetry/communications task. The current draw may be measured in real-time during operation of the device or may be represent a set or programmed value that is predetermined from tests, calculations or otherwise.

$T_{char}$=time spent performing the high drain charging task (e.g., charging capacitors or other shock therapy storage circuits).

$T_{tele}$=time spent performing the high drain telemetry/communications task.

$C_{ss}(n)=\int_{t=0}^{t_n} I_{ss}(t)dt$=Total steady state charge consumption from a starting point to a set point in time (n). The total steady state charge consumption is obtained by integrating current from steady state power usage $I_{ss}(t)$, such as for pacing and running the computer and A/D conversion.

$C_{tele}(n)=I_{tele}*T_{tele}(n)$=Telemetry related charge consumption obtained by multiplying the average current draw during a telemetry task times the time spent performing telemetry.

$C_{char}(n)=I_{char}*T_{char}(n)$=Charging related charge consumption obtained by multiplying the average current draw during a charging task times the time spent performing charging.

$C_{task}(n)=I_{task}*T_{task}(n)$=Total task related charge consumption for all tasks that are tracked by the medical device. The total task related charge consumption is obtained by multiplying the corresponding average current draw during a task times the time spent performing the task, and summing the task related charge consumption for all tasks that are tracked. The total task related charge consumption includes the projected telemetry related charge consumption, charging related charge consumption and all other task related charge consumption (other than steady state charge consumption).

$C_{tot}(n)=C_{SS}(n)+(C_{tele}(n)+C_{char}(n)$=Total charge consumption drawn externally from the battery cell by the device from a set starting point up to a point in time (n) from all charge demands.

BV(n)=Cell voltage measured at a point in time "n". The cell voltage may be measured periodically (e.g., each day) utilizing a voltage measurement circuit with (within) the medical device.

BVest(n)=Projected cell voltage that is determined utilizing a capacity v. voltage model (e.g., a lookup table), where the projected cell voltage is based on the total charge consumption $C_{tot}(n)$.

ED Threshold=Early depletion threshold that defines a tolerance range that the measured and projected cell voltages may vary from one another before declaring an early depletion condition (e.g., BVest(n)−100 mV).

Embodiments may be implemented in connection with one or more battery powered medical device, such as implantable medical devices (IMDs). Non-limiting examples of IMDs include one or more of neurostimulator devices, implantable leadless monitoring and/or therapy devices, left ventricular assist devices, percutaneous heart pump devices, implantable heart assist devices, and/or alternative implantable medical devices. As other examples, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed. Virtual Stimulation Cathode For Use With An implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD may include one or more structural and/or functional aspects of the device(s) described in U.S. Pat. No. 9,138,518 "Percutaneous Heart Pump" and U.S. Pat. No. 7,331,921 "Implantable Heart Assist System", which are hereby incorporated by reference.

Cell Voltage-Capacity Model

FIG. 1 exhibits a predictable cell voltage versus capacity profile for a model battery cell, such as a high quality cell made with chemically pure, predictable constituents. The horizontal axis plots battery capacity expended/discharged in milliamps hours, while the vertical axis plots the cell voltage. The curve in FIG. 1 shows that when the voltage drops to a certain level, the cell has reached the elective replacement indicator (ERI) and ultimately will reach the end of life (EOL), such as in about 6 months for a pacemaker and 3 month for an implantable cardioverter defibrillator. Optionally, voltage measurements may be obtained to determine a cell voltage by connecting a standard load to the battery cell (e.g., a 100 K ohm load; or a load that draws a fixed current; e.g., 30 uA). Once the standard load is applied, a voltage potential across the load can be measured. It is recognized that the voltages or shape of the curve illustrated in FIG. 1 is an example and is not limiting. The voltage-capacity curve is calibrated for average daily background current usage.

In the example of FIG. 1, at the beginning of the battery life (e.g., fully charged, when no capacity has been expended), the battery exhibits an initial voltage of approximately 3200 mV (3.2 V). After being utilized for a period of time, during which the battery expends approximately 200 mA-hours of the initial full charge, the battery voltage drops to about 3 V, where the battery voltage is maintained over a substantial majority of the remaining capacity of the battery until approaching the end of life condition. Prior to reaching an end-of-life condition, the battery voltage begins to drop at an increasing rate (e.g., when the battery has expended approximately 875 mA-hours of the batteries capacity) until reaching a point at which the battery cell has expended about 1250 mA-hours (designated as the early replacement indicator (ERI)). Once the battery voltage reaches the ERI, the battery voltage drops relatively quickly over a relatively small amount of the overall battery capacity (e.g., dropping 300 mV over the discharge of approximately 200 mA-hours). The battery voltage ultimately drops below the EOL voltage (e.g., when approximately 1800 mA-hours of capacity have been utilized). The ERI indicator designates that the battery is sufficiently depleted to warrant battery replacement. In some devices, the ERI indicator may designate that the entire device should be replaced, which may involve explant of an implantable medical device or otherwise. It is recognized that the curve in FIG. 1 is merely one example.

However, simply determining that the cell voltage has dropped to some specified threshold level may not be effective in detecting self-discharge of a cell. As explained herein, methods and systems are provided to monitor a state of discharge of a battery cell and/or a rate of battery depletion in order to detect impending premature battery failure before it happens. For instance, if a pacemaker circuit draws 10 microamperes from a battery having a capacity of 100 microampere-years and delivers 10 microamperes for 9 years, then 90 microampere-years has been consumed and about 10 percent of the 100 microampere-years capacity remains.

The charge usage may be determined in various manners. As an example, battery use can be monitored by continuously integrating a current drawn from the battery. Continuous monitoring may be achieved utilizing a current monitoring device (e.g., a coulometer) to measure the state of discharge. However, current monitoring devices, such as a coulometer, only measure the current externally drawn from the battery. Current monitoring devices do not measure cell internal self-discharge within a battery such as caused by "poke thru" or "lithium metal clusters."

Voltage may be used to monitor the state of discharge of high rate batteries when the current drain is more or less constant. However, when the battery experiences high current use, such as during capacitor reforming or delivering shocks, or high power communication, the battery exhibits a transient voltage drop followed by a transient recovery interval that ends with a slight overshoot in voltage. In some embodiments, the battery voltage may not be used to monitor the state of charge during a transient recovery interval. After a predetermined period of time (e.g., several days to a few weeks), the voltage returns to a steady state level that accurately reflects the state of battery charge.

In accordance with embodiments herein, methods and systems are described for detecting cell internal self-discharge during steady state current drain, as well as during a transient recovery interval of the battery. The methods and systems implement various techniques to declare cell internal self-discharge. The methods and systems not only detect the cell internal self-discharge, but also provide one or more indicators to inform the patient, and/or health care professionals of an early depletion condition and a potential impeding battery failure. Non-limiting examples of warning indicators include vibration and/or sounds emitted by a medical device. Other non-limiting examples include transmitting warnings wirelessly (e.g., Bluetooth, WiFi) to another electronic device, such as a patient's personal digital devices (e.g., cell phones, tablet device, laptop computer, etc.), a bedside monitoring device and the like. The receiving device may then convey a visual and/or audible indication to the patient and/or health care professional.

In accordance with embodiments herein, the methods and systems for detecting self-discharge may be implemented on one or more external devices operating alone or in combination with a portable battery-powered medical device. For example, the methods described herein may be implemented in hardware and/or software loaded on an external device such as the Merlin@Home™ device or a similar device. The method compares measured cell performance against a projected performance saved on the external device, where data space is less limited as compared to memory capacity of implantable medical devices.

Early Depletion Condition Methods

Figure 2:
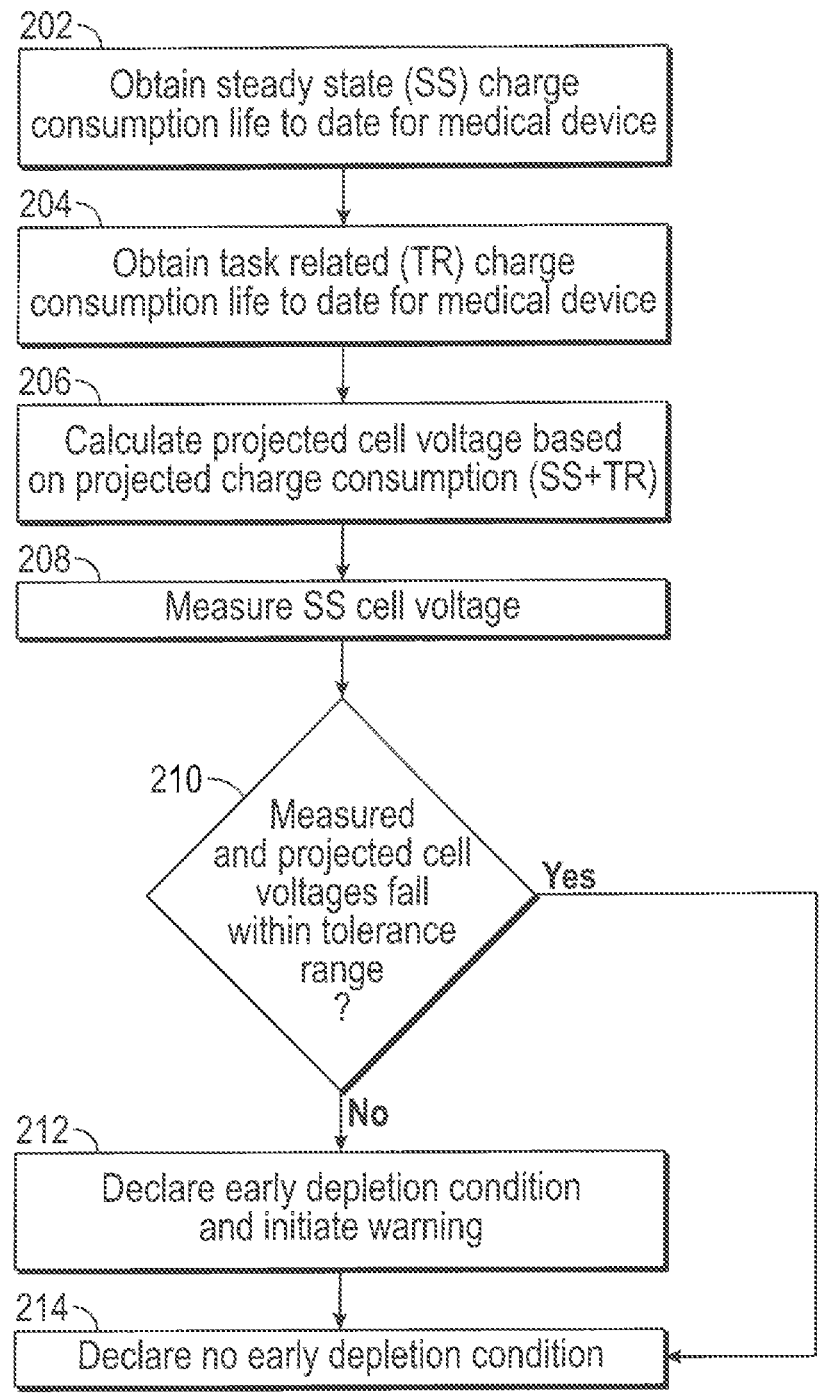
FIG. 2 illustrates a method for determining early battery depletion in accordance with embodiments herein.

FIG. 2 illustrates a method for determining early battery depletion in accordance with embodiments herein. The operations in the method of FIG. 2 may be implemented in whole or in part by a portable medical device carried by a patient, an IMD, an external device, a remote server, a workstation or a combination thereof. At 202, one or more processors of the medical device obtain a steady state consumption $C_{ss}$ that is externally drawn from a battery cell and consumed by the medical device over some select period of time, during which the medical device experiences a steady state demand. For example, the stead state consumption $C_{ss}$ may be a value saved in memory of the medical device that is continuously or periodically updated (independent of any other operations in FIG. 2). As another example, the processor may maintain a SS timer that tracks an amount of time that the medical device has operated in a steady stated since the battery cell was fully charged. The processor may multiply the value of the SS timer by a steady state current draw $I_{ss}(t)$. Optionally, the processor may integrate estimated and/or measured steady state current/charge consumption over the select period of time.

At 204, the one or more processors of the medical device monitor and/or estimate a task related charge that is externally drawn from a battery cell and consumed by the medical device over the select period of time, during which the medical device performs one or more tasks. For example, the task related charge consumption may be a value save d in memory of the medical device that is continuously or periodically updated (independent of any other operations of FIG. 2). As another example, the processor may maintain task related timers for each type of task (e.g., a charging task timer $T_{char}$, telemetry task timer $T_{tele}$). The timers are multiplied by the corresponding current draw and then summed to obtain the total projected task related charge consumption. As another example, the processor may integrate (in real-time) estimated and/or measured task-related current/charge consumption $C_{task}$ attributable to any and all device related tasks.

The estimated and/or measured steady state and task related consumption at 202 and 204 are combined to determine a total charge consumption externally drawn from the battery cell by the medical device. During normal operation, the total charge consumption externally drawn from the battery cell by the medical device would equal the total charge consumption of the battery cell. In accordance with embodiments herein, the operations at 202 and 204 may directly measure the steady state and task related consumption. By way of example, each medical device may include a measurement circuit that is configured to directly measure the current/charge consumed during some period of time, such as the steady state demand and/or during certain tasks (e.g., high drain tasks, low drain tasks). For example, a current monitoring circuit may be provided with (or within) the medical device. The current monitoring circuit directly measures the rate at which current/charge is consumed over each task to directly measure and integrate the total current/charge consumed in connection with the task.

Additionally or alternatively, in accordance with embodiments herein, the operations at 202 and 204 may utilize estimates for the steady state and task related consumption, where the estimates are based on a set of predetermined baseline consumption levels. For example, baseline consumption levels may be assigned to steady state demand and each task, where the baseline consumption level is derived from theoretical calculations. Additionally or alternatively, baseline consumption levels may be derived from tests performed using one or more "baseline" medical devices. For example, a baseline medical device may be directed to perform a task (e.g., capacitor reforming task), during which test equipment measures the current and/or charge that is consumed. The measured current/charge drain is integrated over a duration of the task to obtain a total current/charge that is consumed by the medical device during the task. The test may be repeated by the medical device multiple times and/or may be performed by multiple medical devices, in order to obtain an average baseline consumption level associated with the corresponding task. One or more baseline medical devices may be directed to perform multiple different types of tasks to derive a set of predetermined baseline consumption levels for corresponding tasks.

Thereafter, any and/or all medical devices that are manufactured to the same or similar specification as the baseline medical device(s) (e.g., with the same battery, shocking capacitors, etc.) may be assigned all or a portion of the set of predetermined baseline consumption levels. When an implanted medical device performs a capacitor reforming task, the baseline consumption level for capacitor reforming may be recorded as the amount of current/charge that is consumed, without directly measuring the current/charge consumed. Similarly, each time the medical device performs a capacitor charging task or communications task, the associated baseline consumption level is obtained from memory and recorded as the amount consumed.

Additionally or alternatively, the operations at 202 and 204 may estimate a rate at which current is consumed during tasks and during steady state conditions. The estimated rate may be utilized as a baseline rate of current/charge consumption. Thereafter, when a medical device performs certain tasks or maintains certain conditions (e.g., capacitor reforming task, maintains a steady state operation), the duration of the task/condition is measured and combined (e.g., multiply) with the baseline rate of current/charge consumption to determine the total charge consumption from the battery cell of the device during the select period of time.

The foregoing calculation or measurement may be performed in connection with additional tasks, such as delivering therapy, monitoring signals, communicating with other devices, self-diagnostics, internal maintenance and the like. The foregoing calculation and/or measurement may be performed in connection with delivering shocks or other therapy, performing telemetry operations, transmitting and receiving RF communications, performing projected self-discharge and the like. The calculation and measurements provide a set of baseline consumption levels for predetermined tasks.

At 206, the one or more processors determine a projected cell voltage based on the total charge consumption $C_{tot}$ (steady state and/or task related charge) externally drawn from the battery. For example, the processors may reference a cell voltage versus capacity model, such as the curve illustrated in FIG. 1. As one example, when the charge consumption by the medical device equals 400 mA-hours, at 206, the processors may determine that the projected cell voltage should be approximately 3000 mV. As another example, when the charge consumption (steady state and task related charge) totals approximately 900 mA-hours, the projected cell voltage would be slightly more than 2850 mV.

At 208, the medical device measures a voltage across the battery cell. For example, the voltage may be measured at the terminals of the cell, such as to avoid downstream components within the medical device from affecting the measurement. When the medical device utilizes a feedthrough at an interface between the cell and electronic components within the medical device, the voltage may be measured at battery terminals extending through the feedthrough. Alternatively, when voltage effects of downstream components are not of concern (or are of interest in the measurement), the voltage may be measured at a downstream location, such as at terminals provided on the housing of the medical device. Alternatively, the voltage may be measured at the input contacts of the switch network provided upstream of the terminals on the housing of the medical device. The measurement of voltage may be performed at other locations as well, when interference from other internal components of the medical device are not of concern.

By way of example, when voltage transients are present during a portion of a discharge operation, the processors may delay the measurement operation in order that the cell voltage is measured after the voltage transients have settled. For example, the cell voltage may be measured after the voltage transients have settled down following high current demand conditions. As one example, the cell voltage may be measured after waiting a number of days following a high current demand condition. Additionally or alternatively, the processors may determine the point at which to measure the cell voltage based on a rate of change per unit time in the cell voltage. For example, the processors may monitor the rate of change per unit time (dV/dt) in the cell voltage and wait until the cell voltage dV/dt has settled to a predetermined level (e.g., a sufficiently low level following high current conditions). Once the rate of change per unit time in the cell voltage falls below the predetermined level, the cell voltage may then be considered to represent a steady-state level, in which case the measurement at 208 obtains a steady-state measured cell voltage. As explained hereafter, the steady-state measured cell voltage may be utilized to predict a remaining longevity of the medical device.

At 210, the one or more processors compare the voltage measured at 208 with the projected cell voltage determined at 206. The processors determine whether the measured and projected cell voltages match or fall within a predetermined tolerance range of one another. At 210, when the measured voltage falls below the projected cell voltage by more than the predetermined tolerance range, then it is likely that there is excessive cell internal self-discharge, such as attributable to "lithium clusters" or "poke through". Accordingly, flow moves to 212.

At 212, the one or more processors declare an "early depletion condition" and initiates a warning. The warning provides one or more indicators to inform the patient, and/or health care professionals of an early depletion condition and a potential impeding battery failure. Non-limiting examples of warning indicators include vibration and/or sounds emitted by a medical device. Other non-limiting examples include transmitting warnings wirelessly (e.g., Bluetooth, WiFi) to another electronic device, such as a patient's personal digital devices (e.g., cell phones, tablet device, laptop computer, etc.), a bedside monitoring device and the like. The receiving device may then convey a visual and/or audible indication to the patient and/or health care professional.

Alternatively, when the measured and projected cell voltages match or fall within the predetermined limits, flow moves from 210 to 212. At 212, the one or more processors declare a "no early depletion condition", indicating that the battery cell is operating in an accepted/normal state. The operations of FIG. 2 seek to quantify the change in battery state by identifying abrupt changes in predicted longevity. The operations of FIG. 2 are insensitive to periods of high usage because the battery voltage is ignored for longevity predictions until the battery cell has settled and returned to a steady state voltage.

Figure 3:
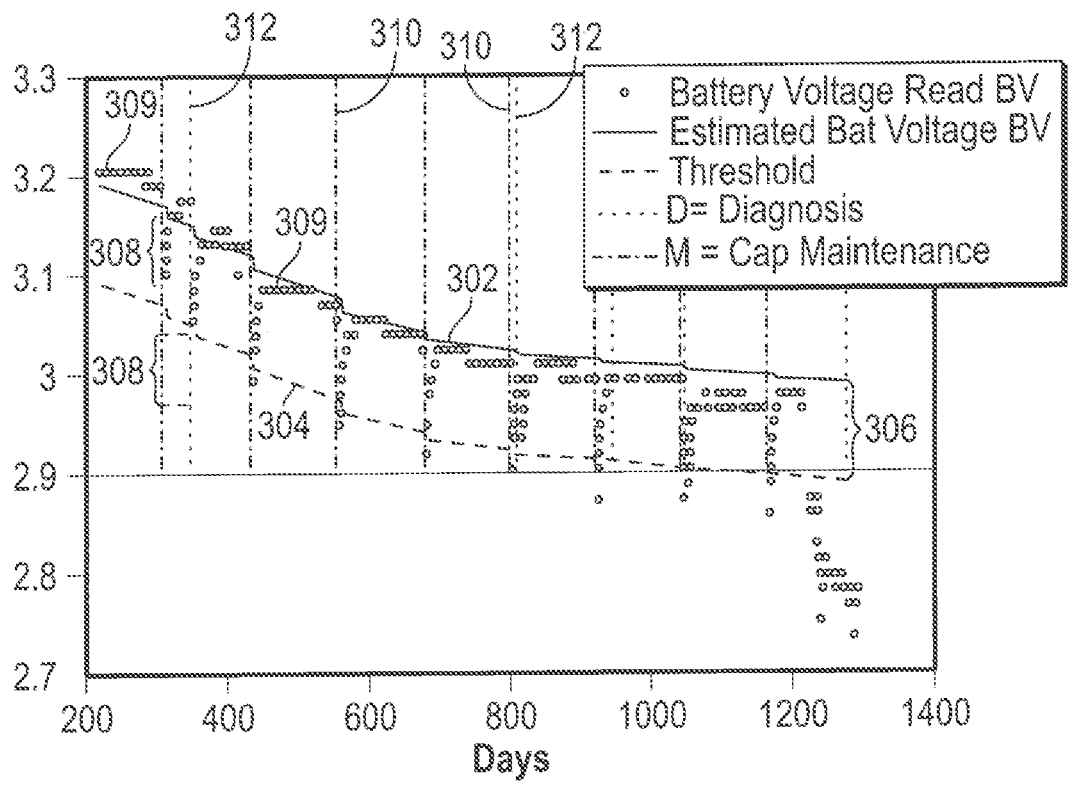
FIG. 3 illustrates curves plotting battery cell voltage versus time (in days) utilized in accordance with embodiments herein.

FIG. 3 illustrates curves plotting battery cell voltage versus time (in days) utilized in accordance with embodiments herein. FIG. 3 illustrates a solid line corresponding to projected cell voltage 302 and a thin dashed line corresponding to a limit 304 for a threshold range 306. A series of dots 308 and wide dashed lines 309 correspond to transient and steady state (SS) measured cell voltage values at various points in time over several years. FIG. 3 includes a first set of vertical lines 310 labeled "M" to denote points in time at which a capacitor maintenance task (e.g., a capacitor reforming task) is performed. FIG. 3 includes a second set of vertical lines 312 labeled "D" to denote points in time at which a therapy task (e.g., a shock and capacitor recharge task) is performed. The capacitor maintenance tasks "M" 310 are performed on a predefined schedule and thus represent one example of a scheduled task. The shock and capacitor recharge tasks "D" 312 are performed on an arbitrary basis based on patient need thus represent one example of a non-scheduled task.

The SS voltage measurements indicated by the wide dashed lines 309 were measured when the battery cell was not undergoing a heavy current usage demand. The transient voltage measurements indicated by the dots 308 were measured when the battery cell was undergoing a heavy current usage demand. The measured voltage may be measured at various points over the life of the medical device (e.g., daily) as the medical device consumes capacity from the battery cell.

The projected cell voltage $BV_{est}$ 302 is estimated based on the method of FIG. 2 utilizing a cell voltage v. capacity model (e.g., lookup curve in FIG. 1) and the total charge consumption $C_{tot}$ determined at 202 and 204. The determination at 210 determines whether the measured cell voltage (308 or 309) falls within the tolerance range 306 and above the limit 304. The SS measured cell voltage 309, at the beginning of battery cell life, is about 3.2V (or 3200 mV). Following each capacitor maintenance M operation, the transient measured cell voltage 308 drops by 0.1V or more to recover to a new SS measured cell voltage that is lower than the last SS measured cell voltage. During the earlier portion of the battery life, the transient measured cell voltage 308 exhibits transient voltage drops that temporarily fall below the limit 304 (e.g., after 400 days of use). However, the voltage recovers to a steady state level above the limit 304 for an extended period of time (e.g., up until about 1200 days of use). The SS measured cell voltage 309 falls below the limit 304 after about 1200 days of use and does not recover to a level above the limit 304, even after transients have settled out. The method of FIG. 2 would declare "no early depletion condition" (at 214), each time the operations of FIG. 2 are performed (e.g., shortly before each scheduled capacitor maintenance task) until about 1200 days of use. Thereafter, the method of FIG. 2 would declare an early depletion condition at 212.

The process described in connection with FIG. 2 estimates a projected cell voltage $BV_{est}(n)$ for a select point in time based on a total charge consumption $C_{tot}(n)$ that is tracked over time. However, the total charge consumption $C_{tot}(n)$ may not always be precise due to factors such as a rate of discharge of the battery, slight individual variations from one battery to another, and the like. Hence, an estimation for the total charge consumption $C_{tot}(n)$ may slightly deviate over time.

Figure 4:
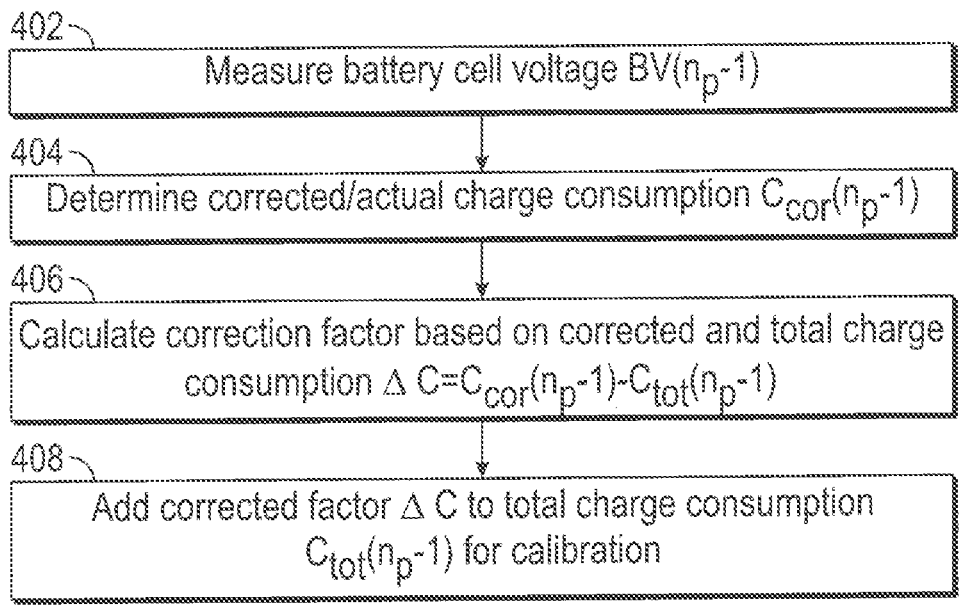
FIG. 4 illustrates a method to perform a recalibration process to periodically correct for differences between the corrected charge consumption $C_{cor}$ and the total charge consumption $C_{tot}(n)$ in accordance with embodiments herein.

FIG. 4 illustrates a method to perform a recalibration process to periodically correct for differences between the corrected charge consumption $C_{cor}$ and the calculated total charge consumption $C_{tot}(n)$ in accordance with embodiments herein. The recalibration process may be performed on a periodic basis, performed in response to triggering activity or otherwise. For example, the calibration process may be performed every 90 to 180 days on the day before a high drain scheduled task (e.g., a capacitor reforming task). Optionally, the recalibration process may be skipped or delayed upon the occurrence of an event triggering a warning, and/or based on the occurrence of a high drain task, such as delivering a shock and recharging the capacitor. The recalibration process may utilize the following equation to calculate the difference $\Delta C$ between the total charge consumption $C_{tot}$ and the corrected charge consumption $C_{cor}$: $C_{cor}(n_p-1)=C_{tot}(n_p-1)+\Delta C$, where $n_p$ corresponds to a point in time at which the battery cell voltage drops to a negative peak $n_p$ during the high drain scheduled task (e.g., capacitor maintenance/reforming).

At 402, one or more processors of the medical device measures the battery voltage to obtain a measured cell voltage $BV(n_p-1)$. The designator $(n_p-1)$ corresponds to a point in time preceding the high drain scheduled task by a select interval (e.g., 1 day), and thus preceding the point in time at which the battery cell voltage drops to the negative peak $(n_p)$. For example, when the high drain scheduled task is set to occur on day #, then the designator $(n_p-1)$ corresponds to a point in time approximately 24 hours (or some other fixed interval) before the time set for the high drain scheduled task. As a further example, the battery may be measured on a predetermined day before capacitor maintenance (M) designated as day, $n_p-1$.

At 404, the one or more processors use the measured cell voltage, $BV(n_{p-1})$ to find a present value for the corrected charge consumption $C_{cor}(n_{p-1})$ based on a lookup model or curve represented in FIG. 1. At 406, the one or more processors use the corrected charge consumption and total charge consumption $C_{cor}$, at the time $n_{p-1}$ to calculate a correction factor $\Delta C=C_{cor}(n_p-1)-C_{tot}(n_p-1)$. At 408, the one or more processors stores the correction factor $\Delta C$ to be used with subsequent total charge consumptions $C_{tot}$. The correction factor $\Delta C$ is then used (added) during subsequent iterations through the operations of FIG. 2 to correct each subsequent value for the total charge consumption $C_{tot}$ that is tracked by the device, such as according to the following equation: $C_{cor}(n_{p-1})=C_{tot}(n_{p-1})+\Delta C$. For the next 90 days the correction factor, $\Delta C$, is added to the total charge consumption $C_{tot}(t)$ when estimating the corrected charge consumption $C_{cor}(t)$ is then used to estimate a corrected cell voltage $BV_{cor}(t)$ using FIG. 1. A corrected threshold is defined based on the corrected cell voltage. As one non-limiting example, the corrected threshold may be $\text{Threshold}_{corr}=BV_{cor}(t)-100$ mV. If the actual battery voltage drops below threshold, this signals an "out of bounds" condition and is indicative of battery internal self-discharge. Transient drops in voltage after shock or after capacitor maintenance are considered normal and ignored.

Returning to FIG. 3, the projected cell voltage 302 includes a step down in voltage following each scheduled capacitor maintenance task, which corresponds to the points in time at which the recalibration of FIG. 4 is performed. Each time the projected cell voltage 302 steps down, the limit 304 for the tolerance range 306 also steps down.

The operations described above in connection with FIGS. 2 and 4 measure cell voltage at steady state points in operation. However, following heavy usage tasks, the battery cell enters a transient state for an extended period of time (e.g., several days). Accordingly, embodiments herein are described that account for the transient state. As one example, when cell voltage is measured while in a transient state, a low pass filter may be applied to obtain projected cell voltages as the battery cell recovers from the negative peak voltage.

Figure 5:
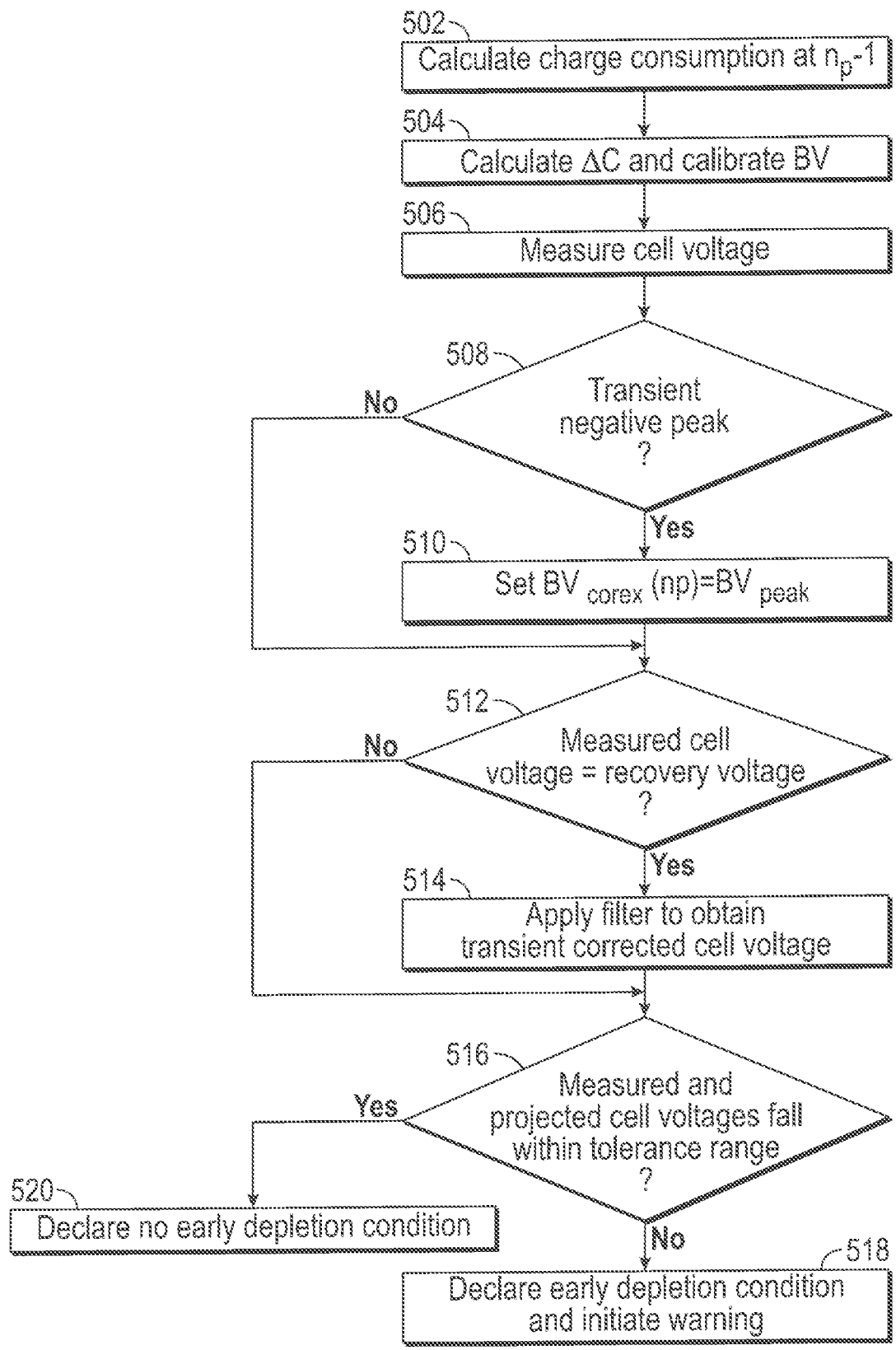
FIG. 5 illustrates a method for determining premature battery depletion, during periods of time when the battery cell is recovering from a transient negative voltage, in accordance with embodiments herein.
Figure 6:
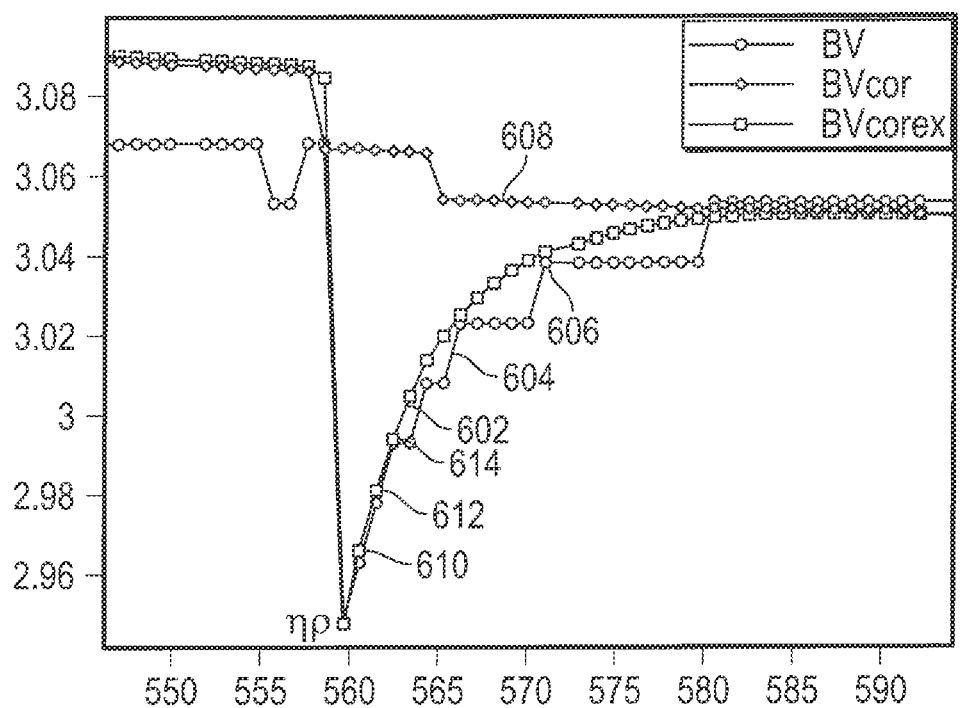
FIG. 6 illustrates a graph plotting voltage along the vertical axis and time (in days) along the horizontal axis in accordance with embodiments herein.

FIG. 5 illustrates a method for determining premature battery depletion, during periods of time when the battery cell is recovering from a transient negative voltage, in accordance with embodiments herein. The operations in the method of FIG. 5 may be implemented in whole or in part by a portable medical device carried by a patient, an IMD, an external device, a remote server, a workstation or a combination thereof. The operations of FIG. 5 are described in connection with FIG. 6. FIG. 6 illustrates a graph plotting voltage along the vertical axis and time (in days) along the horizontal axis. A solid line 602 illustrates a corrected cell voltage that is been corrected for the transient behavior following the negative voltage drop, BVcorex. A solid line 604 illustrates the measured cell voltage with each data point 606 corresponding to a point in time at which the cell voltages measured, BV. A dashed line 608 illustrates a cell voltage that does not account for the transient negative voltage drop. In the example illustrated in FIG. 6, the dashed line 608 is the corrected cell voltage $BV_{cor}$ estimated using $C_{cor}(n_{p-1})=C_{tot}(n_{p-1})+\Delta C$ as described above.

Returning to the operations of FIG. 5, at 502, the one or more processors implement the operations of FIG. 2 to calculate the charge consumption at the point in time preceding a scheduled task, such as at $n_p-1$. At 504, the one or more processors implements the operation of FIG. 4 in order to calculate $\Delta C$ and two recalibrate the total charge consumption, such as at $n_p-1$. At 506, the one or more processors measures cell voltage and at 508 determines whether the battery cell is undergoing a transient causing the cell voltage to drop to a negative peak voltage. When the measured voltage corresponds to the negative peak voltage, flow moves to 510 where the transient corrected cell voltage $BV_{corex}(n_p)$ is set to equal the negative cell voltage peak $BV_{peak}$ is set. Otherwise flow skips to 512. At 512, the one or more processors determine whether the measured cell voltage corresponds to a recovery voltage after the negative peak voltage during the recovery phase. When the measured cell voltage corresponds to a recovery voltage, flow moves to 514.

At 514, the one or more processors apply the first order lay exponential digital filter to obtain a transient corrected cell voltage. At 508 and 512, when the measured cell voltage does not exhibit a transient negative peak or recovery voltage, the filter applied at 514 is by passed. With reference to FIG. 6, when the measured cell voltage corresponds to point 610, the corrected cell voltage may be determined utilizing the following formula: $BV_{corex}(n_p+1)=0.15*BV_{cor}(n_p+1)+0.85*BV_{peak}$. When the measured cell voltage corresponds to point 612, the corrected cell voltage is determined utilizing the following formula: $BV_{corex}(n_p+2)=0.15*BV_{cor}(n_p+1)+0.85*BV_{corex}(n_p+1)$. When the measured cell voltage corresponds to point 614, the corrected cell voltage is determined utilizing the following formula: $BV_{cores}(n_p+3)=0.15*BV_{cor}(n_p+3)\ 0.85*BV_{corex}(n_p+2)$. It is recognized that the above example is one type of filter that may be applied. Alternative types of filters may be applied to estimate the exponential shape of the cell voltage when recovering during a transient state.

At 516, the one or more processors compare the voltage measured with the projected cell voltage. The processors determine whether the measured and projected cell voltages match or fall within a predetermined tolerance range of one another. When the measured voltage falls below the projected cell voltage by more than the predetermined tolerance range, then it is likely that there is excessive cell internal self-discharge, such as attributable to "lithium clusters" or "poke through". Accordingly, flow moves to 518. At 518, the one or more processors declare an early depletion condition and indicates a warning. Alternatively, when the measured and projected cell voltages match or fall within the predetermined tolerance range, flow moves from 516 to 520. At 520, the one or more processors declare a no early depletion condition, or an accepted/normal condition.

In the foregoing embodiments, methods and systems are described that identify an early depletion condition when the cell voltage decreases by a predetermined limit/level below a threshold voltage, representing a projected cell voltage. However, in certain instances, the measured cell voltage may not deviate (by an amount greater than the limit) from the projected threshold voltage until a relatively short time before an impending battery cell failure. However, other characteristics of the battery voltage may be monitored to identify impending cell failures. For example, a rate of change in the cell voltage over time may be utilized to initiate an early depletion condition. Multiple cell voltage measurements may be recorded over an extended period of time and changes there between identified. The rate of change may be analyzed in various manners to identify an early depletion condition. A data collection on the rate of change history provide the failure diagnostics of the battery depletion.

Figure 7:
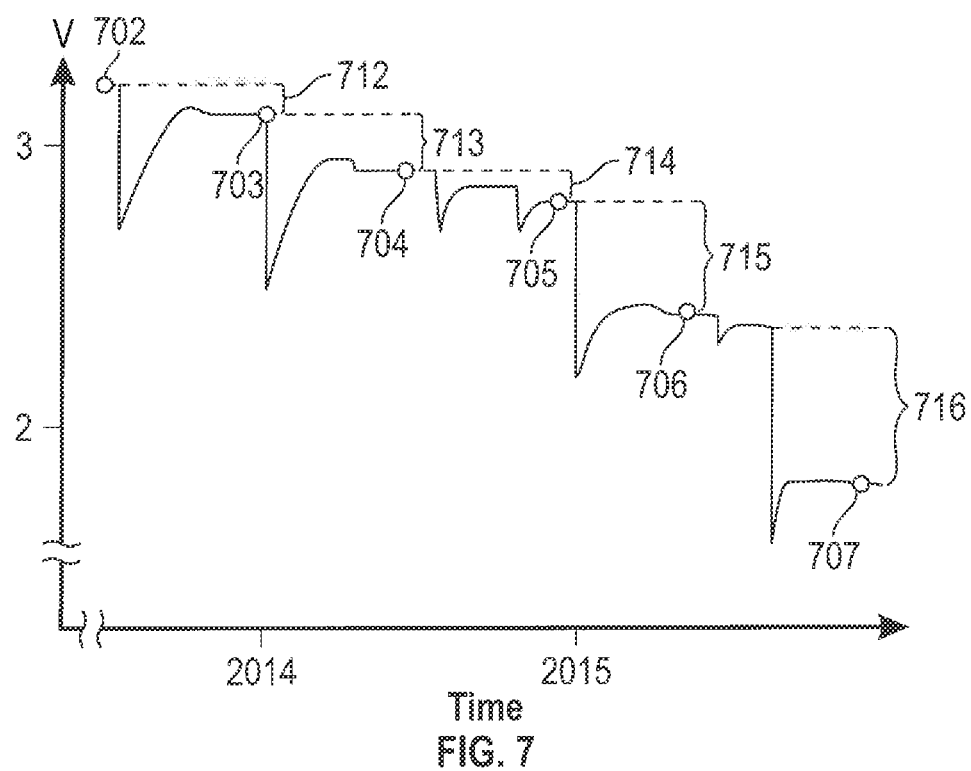
FIG. 7 illustrates a graph plotting battery voltage versus time over multiple years in accordance with embodiments herein.

FIG. 7 illustrates a graph plotting battery voltage versus time over multiple years. The horizontal axis illustrates measurement times over multiple years, while the vertical axis illustrates battery voltage that is automatically measured periodically when the medical device is in an unloaded state. By way of example, battery voltage may be measured on consecutive days, weeks or months. The example of FIG. 7 illustrates voltage drops that occur over time without any high usage events occurring, such as shocks, capacitor reforming, or other high current drain tasks. The rate of change between past and present successive cell voltage measurements is analyzed in accordance with the operations of FIG. 8.

Figure 8:
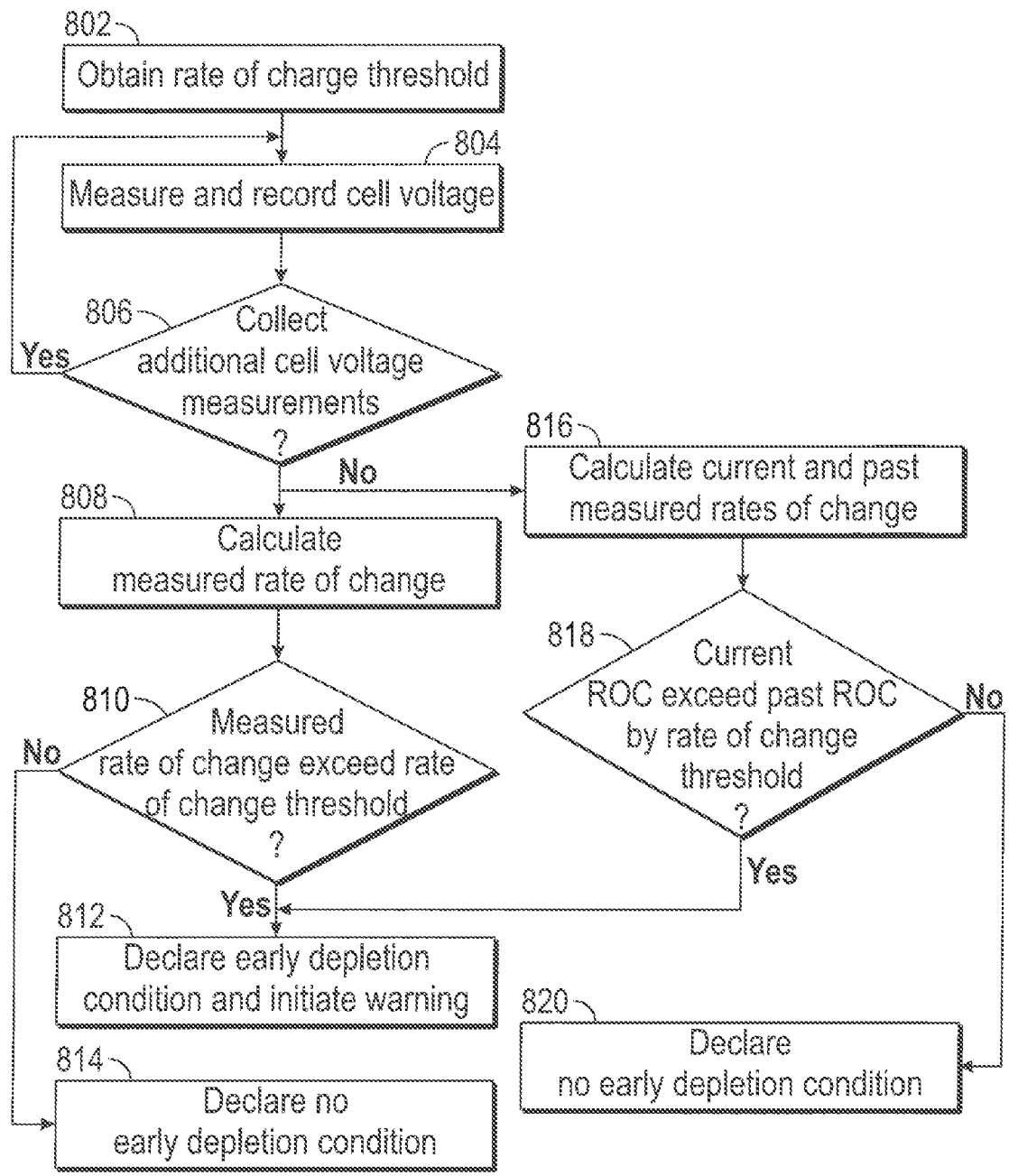
FIG. 8 illustrates a method for detecting a battery depletion condition based on voltage rate changes of a battery cell in accordance with embodiments herein.

FIG. 8 illustrates a method for detecting a battery depletion condition based on voltage rate changes of a battery cell in accordance with an alternative embodiment herein. The method of FIG. 8 may be used in combination with or in place of other battery depletion methods described herein. At 802, one or more processors obtain a rate change threshold indicative of a limit or tolerance range that the rate of change that is accepted before declaring an early depletion condition. In accordance with embodiments herein, the rate of change threshold obtained at 802 may be a constant threshold preprogrammed at the time of manufacture, at the time of implant or thereafter. Additionally or alternatively, the rate of change threshold may include a set of rate of change thresholds that may be used for different conditions. For example, first and second rate of change thresholds may be defined for light versus heavy current usage conditions. As another example, first and second rate of change thresholds may be defined for battery cells that are early versus late in the life of the battery. The rate of change threshold may also vary based on the day to day current drain level, as well as on other factors. For example, a battery cell at a middle point in the cell life may exhibit one rate of change when the current drain is at a typical level. For example, when the current drain is 10-15 microamps on average during steady-state use, at midlife, the cell may be projected to exhibit a 12 mV per month drop in cell voltage. At 804, the medical device measures a voltage across the battery cell and saves the voltage measurement along with the date and time at which the measurement was performed. Additional information may also be stored such as the operating condition of the medical device, other tasks currently or recently being performed and the like.

At 806, the one or more processors determine whether additional cell voltage measurements are to be collected before continuing with the operations of FIG. 8. When additional cell voltages are to be recorded, flow returns to 804, where the medical device waits a predetermined period of time (e.g., until the next periodic voltage measurement cycle, until the triggering activity occurs, etc.). The operations at 804 and 806 are repeated until a sufficient plurality of cell voltage measurements are obtained. Once a sufficient plurality of cell voltage measurements are collected, flow moves to 808. At 808, the plurality of cell voltage measurements are analyzed to identify a measured rate of change (dV/dt). With reference to FIG. 7, cell voltage measurements are noted at 702-707 which are collected over a 3 year period. After each of the cell voltage measurements 703-707, a difference is calculated between the corresponding measurements to obtain measured rates of change 712-716 (dV/dt). For example, the measured rate of change 713 is approximately 0.2V, while the measured rate of change (dV/dt) 714, 715 and 716 are 0.1V, 0.4V and 0.55V, respectively. As one example, the measured rate of change (dV/dt) may represent the difference between two successive voltage measurements divided by the time interval there between. Additionally or alternatively, the measured rate of change may represent an average rate of change (dV/dt) over multiple cell voltage measurements (e.g., measurements collected over a few days, months and the like).

At 810, the one or more processors compare the measured rate of change with the rate of change threshold. When the measured rate of change exceeds the rate of change threshold, flow moves to 812, where an early depletion condition is declared and a warning is initiated. Alternatively, when the measured rate of change does not exceed the rate of change threshold, flow moves to 814, where no early depletion condition is declared. In the example of FIG. 7, the threshold may be 0.4V, such that the measured rates of change 712-714 are found to be normal, while the measured rates of change 715-716 are declared to indicate an early depletion condition. The foregoing process of FIG. 8 allows an additional type of analysis to be applied in place of, or in addition to, the determinations based on cell voltage described herein. When a negative rate of change, dV/dt, is greater than projected, the excessive negative rate of change represents an indicator of cell interval self-discharge.

In the foregoing example, the rate of change threshold may be set to 20 mV per month at a midpoint in a life of the battery cell. When the measured rate of change (determined at 808) is in excess of 20 mV/month, the method may determine that there is a higher than expected rate of capacity drop, potentially due to self-discharge.

FIG. 8 illustrates an additional analysis that may be performed in place of, or in addition to, the operations at 808 and 810. At 816, the one or more processors obtain current and past measured rates of change. For example, a past measured rate of change may be for a predetermined period of time (e.g., one month earlier, the change over a one-month period a year earlier, the change over one or more weeks at a fixed time in the past, and the like). The current measured rate of change may be for a predetermined period of time leading up to the present analysis (e.g., the current month, the current week, etc.). In the example of FIG. 7, the past and current measured rates of change may be 712 (0.2V0 and 716 (0.55V).

At 818, the one or more processors compare the current and past measured rates of change to determine whether the current rate of change exceeds the past rate of change by a rate of change threshold (e.g., a predetermined factor). For example, at 818, the processors may determine whether the current rate of change exceeds the past rate of change by a rate of change threshold that equals a factor of two or more of the past rate of change. When the current rate of change increases by the predetermined threshold/factor over the past rate of change, this is an indication of a problem cell self-discharge. With reference to FIG. 7, the ratio of the rates of change 712 and 716 would be greater than 2. As one example, the operations at 816 and 818 may be performed at certain points in time during the life of the battery cell and/or when the measured cell voltage falls below a threshold (e.g., below 2.8 V). When a cell voltage falls below a threshold, thereafter, sudden increases in the rate of change in the measured cell voltage may be considered indicative that the battery cell is nearing an ER point or end-of-life. Flow branches between 812 and 820 based on the decision at 818. At 820, a no early depletion condition is declared. At 812, an early depletion condition is declared and a warning is initiated.

The analysis of FIG. 8 may be utilized with short-term averaging and/or long-term averaging for the rate of change, dV/dT. For example, a monthly long-term average trend may be monitored, as well as a short-term average trend (e.g., for a few days). As a further example, when monitoring a negative steady-state rate using monthly long-term average trends, a deviation in a two day moving average short-term trend (that exceeds a threshold) may be indicative of self-discharge.

Figure 9:
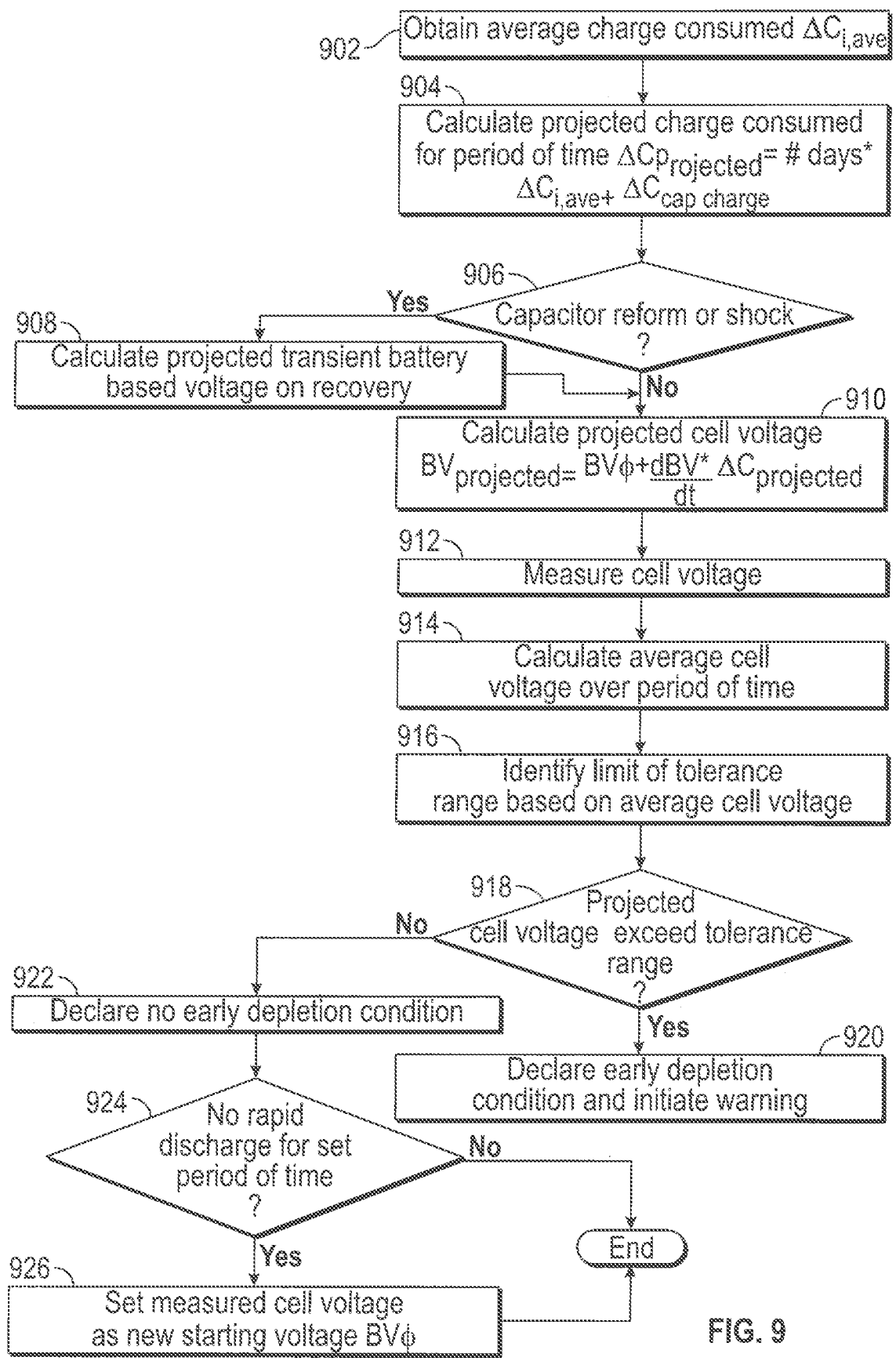
FIG. 9 illustrates a method for determining premature battery depletion in accordance with embodiments herein.

FIG. 9 illustrates a method for determining premature battery depletion in accordance with an alternative embodiment herein. The operations in the method of FIG. 9 may be implemented in whole or in part by a portable medical device carried by a patient, an external device, a remote server, a workstation or a combination thereof. The method of FIG. 9 may be implemented in combination with, or in place of, other methods described herein. At 902, one or more processors obtain an average charge consumption $\Delta C_{i,ave}$ drained from the battery cell for a predetermined period of time. For example, a charge consumption device, such as a coulometer, may be used to measure the average charge consumption $\Delta C_{i,ave}$ from the battery cell.

At 904, the one or more processors calculate a total projected charge consumed for the predetermined period of time or another interval. For example, the period of time may be multiple days (e.g., 15 days, 90 days). To calculate the total projected charge consumed, the average charge drain $\Delta C_{i,ave}$ is multiplied by the number of days for the period of time of interest. For example, the total projected charge consumed following the voltage drop for the next 15 days is estimated using the projected rate of charge drain using the average daily coulometer charge, $\Delta C_{i,ave}$ multiplied by the number of days post voltage drop plus the charge consumed by charging the capacitors: $\Delta C_{projected}=Days*\Delta C_{i,ave}+\Delta C_{cap\text{-}charge}$. In addition, the projected total charge may include any charge consumed for other tasks, such as the charge $\Delta C_{cap\text{-}charge}$ to recharge capacitors in an IMD.

At 906, the one or more processors determine whether certain types of tasks (e.g., heavy current usage tasks) have been performed that may impose heavy current usage on the battery cell. For example, the decision at 906 may determine whether a capacitor reform task has been performed, whether a shocking therapy has been delivered, whether a wireless communications task has been performed and the like. When a heavy current usage task is identified at 906, flow moves to 908. Otherwise, flow moves to 910.

At 908, the one or more processors calculate a projected transient voltage based on an exponential recovery curve. As explained herein, following heavy current usage tasks, the instantaneous voltage exhibited across the cell drops significantly below the steady-state voltage for some period of time. After the cell voltage drops, the cell voltage recovers/ increases over time along a recovery pattern resembling an exponentially increasing curve. The exponential curve has a shape that is a function of a time constant (e.g., corresponding to the number of days). As one non-limiting example, the recovery pattern may have an exponential curve defined by $Y=\exp^{-(n/m)}$, where "m" represents the time constant in days and "n" represents the number of says since the capacitor charge task giving rise to the voltage drop. The recovery pattern may have various shapes. As another example, the first order exponential filter described in connection with FIG. 5 may be utilized.

Figure 10:
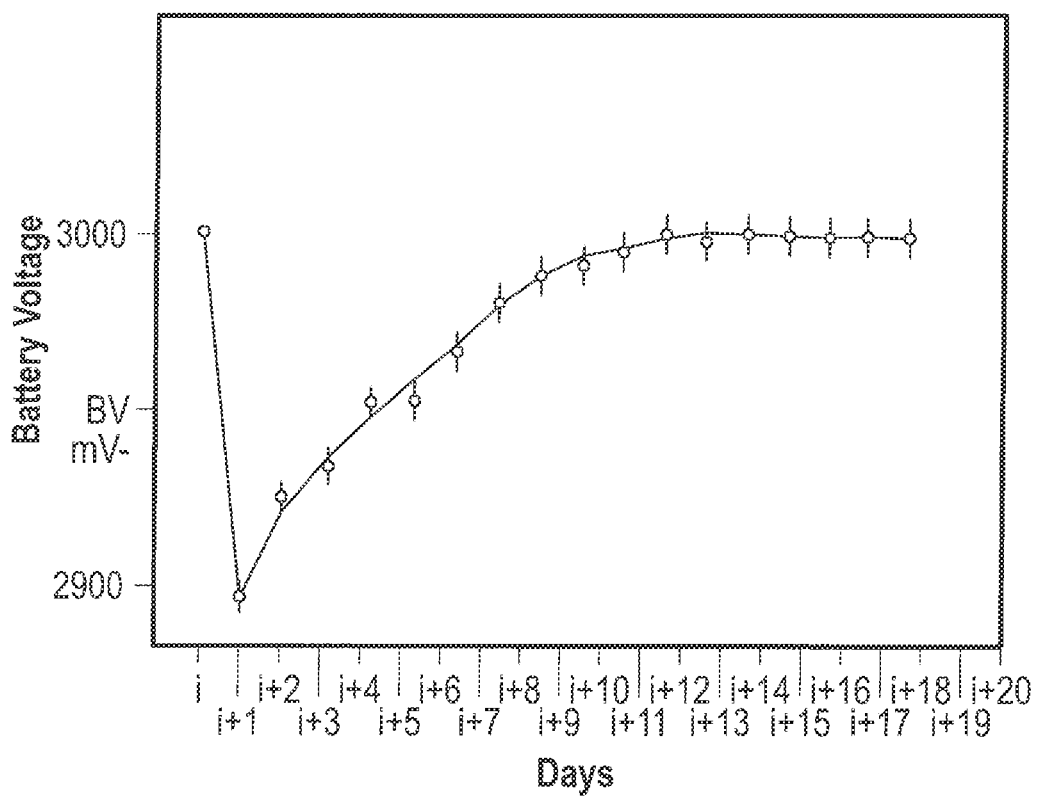
FIG. 10 shows an example of a cell voltage exhibited by a medical device following a battery voltage drop due to charging a capacitor for either capacitor reform or a therapeutic shock in accordance with embodiments herein.

FIG. 10 shows an example of a cell voltage exhibited by a medical device following a battery voltage drop due to charging a capacitor for either capacitor reform or a therapeutic shock. The point BV0 corresponds to the initial cell voltage, while the point $BV_t$ corresponds to the lowest voltage level to which the cell voltage drops following capacitor charge (e.g., in connection with capacitor reforming, delivery of a therapy). As shown in FIG. 10, the cell voltage progressively recovers over multiple days (e.g., 15 days) following the capacitor charging task. During the interval following the capacitor charge task and before the cell voltage fully recovers, an intermediate recovery voltage may be calculated based on the voltage recovery pattern. The intermediate recovery voltage corresponds to the days between the capacitor charge task (e.g., on day number #1) and a current day (e.g., day 5, 10, 15). For example, the voltage recovery pattern may be defined by the equation: $BVi=BV_{projected}+[(BV_t-BV_{projected}]*\exp^{-(n/4)}$ where 4 represents the time constant (in days) and n represents the current day following the capacitor charge task.

Figure 11:
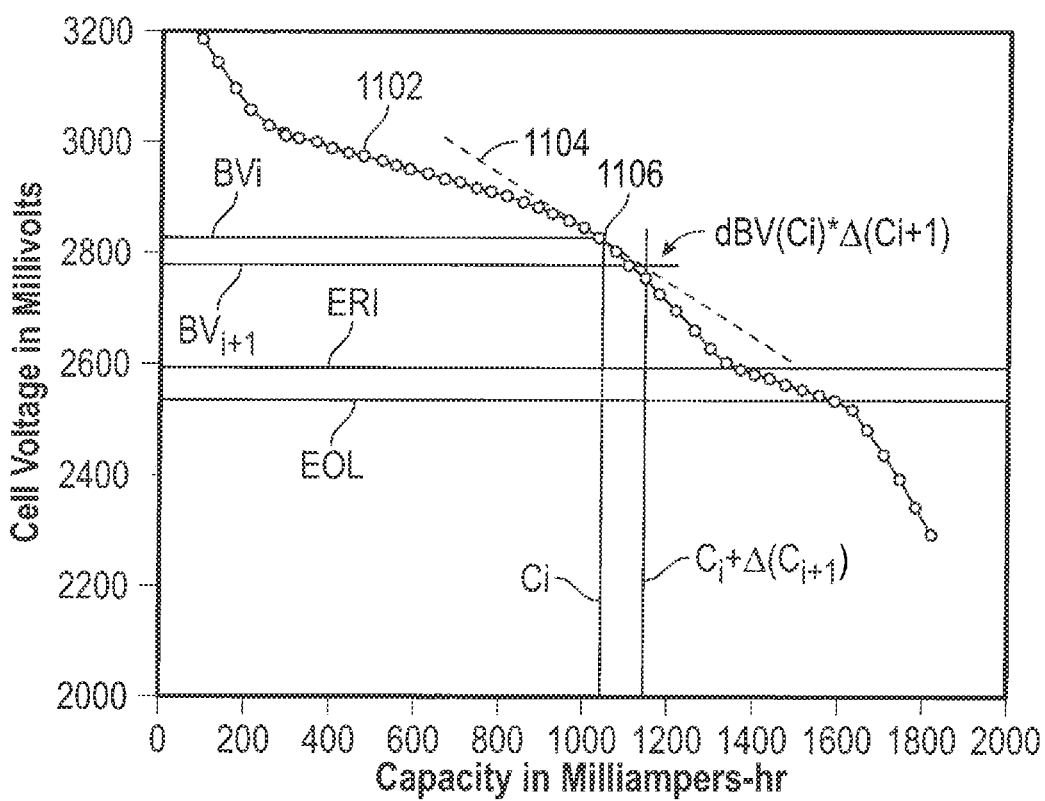
FIG. 11 illustrates a voltage versus capacity curve for a battery cell utilized in accordance with embodiments herein.

FIG. 11 illustrates a voltage versus capacity curve for a battery cell utilized in accordance with embodiments herein. The curve 1102 has slope 1104 at each point 1106. The slope 1104 is used in accordance with the method of FIG. 9 to calculate a projected cell voltage.

Returning to FIG. 9, flow moves to 910 where the one or more processors calculate the projected cell voltage based on an initial cell voltage, a cell voltage rate of change and the total projected charge consumed for the period of time. For example, the projected cell voltage $BV_{projected}$ may be recalculated using the following formula: $BV_{projected}=BV0+\{dBV/dC|_{Co}\}*\Delta C_{projected}$, where $\{dBV/dC|_{Co}\}$ is estimated by taking the derivative of the battery voltage versus charge curve shown in FIG. 11 at the point corresponding to the initial cell voltage $BV_i$. In the example of FIG. 11, the derivative corresponds to the slope 1104 at point 1106.

At 912, the medical device measures the cell voltage. At 914, the one or more processors calculate an average cell voltage over a desired period of time. For example, the measured cell voltage may be averaged over multiple days, multiple hours, longer or shorter periods of time. At 916, the one or more processors identify a limit for a tolerance range based on the average cell voltage. The limit for the tolerance range represents an amount that the projected cell voltage may vary from the average measured cell voltage, before determining an indication of an early depletion condition. At 918, the one or more processors determine whether the projected cell voltage exceeds the limit for the tolerance range. When the projected cell voltage exceeds the limit for the tolerance range, flow moves to 920, where an early depletion condition is declared by the processors and a warning is initiated. When the projected cell voltage does not exceed the limit for the tolerance range, flow moves to 922. At 922, the processors declare a no early depletion condition.

At 924, the one or more processors determine whether a rapid discharge has occurred within a predetermined set period of time. For example, the period of time may represent a few days, such as 15 days. When a rapid discharge has occurred within the most recent set period of time, the process ends without resetting the starting voltage. Alternatively, when a rapid discharge has not occurred within the most recent set period of time, flow moves to 926. At 926, the one or more processors set the current measured cell voltage as the new starting voltage BV0, that is used in subsequent calculations of the projected cell voltage (as determined at 908 and 910).

Implantable Medical Device

Figure 12:
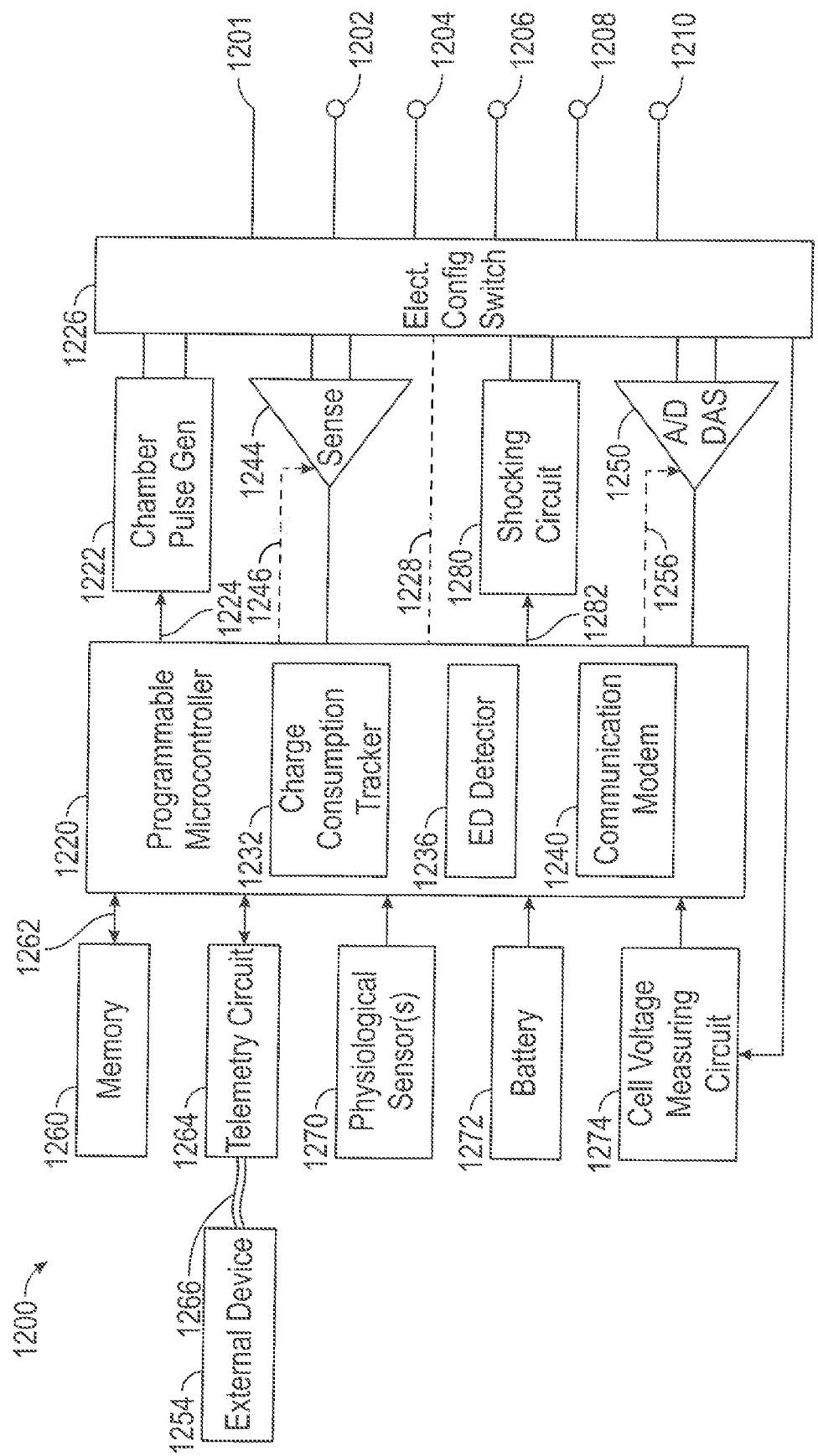
FIG. 12 shows an exemplary IMD that is implanted into the patient as part of the implantable cardiac system in accordance with embodiments herein.

FIG. 12 shows an exemplary IMD 1200 that is implanted into the patient as part of the implantable cardiac system. The IMD 1200 has a housing 1201 to hold the electronic/computing components. The housing 1201 (which is often referred to as the "can", "case", "encasing", or "case electrode") may be programmably selected to act as the return electrode for certain stimulus modes. Housing 1201 further includes a connector (not shown) with a plurality of terminals 1202, 1204, 1206, 1208, and 1210. The terminals may be connected to electrodes that are located directly on the housing of the IMD 1200 and/or connected to one or more leads that are located at various locations within and about the heart. The type and location of each electrode may vary. The IMD 1200 includes a programmable microcontroller 1220 that controls various operations of the IMD 1200, including cardiac monitoring and stimulation therapy. Microcontroller 1220 includes a microprocessor (or equivalent control circuitry), RAM and/or ROM memory, logic and timing circuitry, state machine circuitry, and I/O circuitry.

The microcontroller 1220 includes a charge consumption tracker 1232, an early depletion detector 1236 and other logic to perform the methods described herein. The charge consumption tracker 1232 tracks steady state and device related tasks performed by the IMD and based thereon determines a steady state charge consumption life to date for the medical device and task related charge consumption life to date for the medical device. The charge consumption tracker 1232 performs the various charge consumption related operations described throughout.

The early depletion detector 1236 declares an early depletion condition based on a relation between measured and projected cell voltages or other unexpected behavior of the battery voltage such as sudden unscheduled voltage drop not due to normal operation. The microcontroller 1220 calculates projected cell voltage based on charge consumption, while the early depletion detector 1236 compares the measured and projected cell voltages to determine whether the difference there between falls within a tolerance range. Based on the relation between the measured and projected cell voltages, the early depletion detector 1236 declares an early depletion condition and initiates a warning operation, or declares no early depletion condition and records related information.

The IMD 1200 further includes a pulse generator 1222 that generates stimulation pulses for delivery by one or more electrodes coupled thereto. The pulse generator 1222 is controlled by the microcontroller 1220 via control signal 1224. The pulse generator 1222 is coupled to the select electrode(s) via an electrode configuration switch 1226, which includes multiple switches for connecting the desired electrodes to the appropriate I/O circuits, thereby facilitating electrode programmability. The switch 1226 is controlled by a control signal 1228 from the microcontroller 1220. In the example of FIG. 12, a single pulse generator 1222 is illustrated. Optionally, the IMD 1200 may include multiple pulse generators, similar to pulse generator 1222, where each pulse generator is coupled to one or more electrodes and controlled by the microcontroller 1220 to deliver select stimulus pulse(s) to the corresponding one or more electrodes.

Microcontroller 1220 is includes various modules to implement the functionality of the IMD 1200. For example, the microcontroller 1220 controls the timing of the stimulation pulses (e.g., pacing rate, atrio-ventricular (AV) delay, atrial interconduction (A-A) delay, or ventricular interconduction (V-V) delay, etc.). Microcontroller 1220 detects arrhythrnmia conditions and may review and analyze one or more features of the morphology of cardiac signals. Although not shown, the microcontroller 1220 may further include other dedicated circuitry and/or firmware/software components that assist in monitoring various conditions of the patient's heart and managing pacing therapies.

The IMD 1200 is further equipped with a communication modem (modulator/demodulator) 1240 to enable wireless communication with other devices, implanted devices and/or external devices. In one implementation, the communication modem 1240 may use high frequency modulation of a signal transmitted between a pair of electrodes. As one example, the signals may be transmitted in a high frequency range of approximately 120-80 kHz, as such signals travel through the body tissue and fluids without stimulating the heart or being felt by the patient. The communication modem 1240 may be implemented in hardware as part of the microcontroller 1220, or as software/firmware instructions programmed into and executed by the microcontroller 1220. Alternatively, the modem 1240 may reside separately from the microcontroller as a standalone component.

The IMD 1200 includes sensing circuitry 1244 selectively coupled to one or more electrodes that perform sensing operations, through the switch 1226 to detect the presence of cardiac activity in the right chambers of the heart. The sensing circuitry 1244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 1202 to sense low amplitude signal characteristics of atrial fibrillation. Switch 1226 determines the sensing polarity of the cardiac signal by selectively closing the appropriate switches. In this way, the clinician may program the sensing polarity independent of the stimulation polarity.

The output of the sensing circuitry 1244 is connected to the microcontroller 1220 which, in turn, triggers or inhibits the pulse generator 1222 in response to the absence or presence of cardiac activity. The sensing circuitry 1244 receives a control signal 1246 from the microcontroller 1220 for purposes of controlling the gain, threshold, polarization charge removal circuitry (not shown), and the timing of any blocking circuitry (not shown) coupled to the inputs of the sensing circuitry.

In the example of FIG. 12, a single sensing circuit 1244 is illustrated. Optionally, the IMD 1202 may include multiple sensing circuit, similar to sensing circuit 1244, where each sensing circuit is coupled to one or more electrodes and controlled by the microcontroller 1220 to sense electrical activity detected at the corresponding one or more electrodes. The sensing circuit 1244 may operate in a unipolar sensing configuration or in a bipolar sensing configuration.

The IMD 1200 further includes an analog-to-digital (A/D) data acquisition system (DAS) 1250 coupled to one or more electrodes via the switch 1226 to sample cardiac signals across any pair of desired electrodes. The data acquisition system 1250 is configured to acquire intracardiac electrogram signals, convert the raw analog data into digital data, and store the digital data for later processing and/or telemetric transmission to an external device 1254 (e.g., a programmer, local transceiver, or a diagnostic system analyzer). The data acquisition system 1250 is controlled by a control signal 1256 from the microcontroller 1220.

The microcontroller 1220 is coupled to a memory 1260 by a suitable data/address bus 1262. The programmable operating parameters used by the microcontroller 1220 are stored in memory 1260 and used to customize the operation of the IMD 1200 to suit the needs of a particular patient. The operating parameters of the IMD 1200 may be non-invasively programmed into the memory 1260 through a telemetry circuit 1264 in telemetric communication via communication link 1266 with the external device 1254. The telemetry circuit 1264 allows intracardiac electrograms and status information relating to the operation of the IMD 1200 (as contained in the microcontroller 1220 or memory 1260) to be sent to the external device 1254 through the established communication link 1266.

The IMD 1200 can further include one or more physiologic sensors 1270. Such sensors are commonly referred to as "rate-responsive" sensors because they are typically used to adjust pacing stimulation rates according to the exercise state of the patient.

A battery 1272 provides operating power to all of the components in the IMD 1200. The battery 1272 is capable of operating at low current drains for long periods of time, and is capable of providing high-current pulses (for capacitor charging) when the patient requires a shock pulse (e.g., in excess of 2 A, at voltages above 2 V, for periods of 120 seconds or more). The battery 1272 also desirably has a predictable discharge characteristic so that elective replacement time can be detected. As one example, the unit 1200 employs lithium/silver vanadium oxide batteries.

The IMD 1200 includes a cell voltage measuring circuit 1274 is configured to measure the voltage across the battery cell as explained herein.

The IMD 1200 may be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 1220 further controls a shocking circuit 1280 by way of a control signal 1282. The shocking circuit 1280 generates shocking pulses of low (e.g., up to 0.5 joules), moderate (e.g., 0.5-10 joules), or high energy (e.g., 1211 to 40 joules), as controlled by the microcontroller 1220. Such shocking pulses are applied to the patient's heart through shocking electrodes. It is noted that the shocking circuit 1280 is optional and may not be implemented in the IMD, as the various slave pacing units described below will typically not be configured to deliver high voltage shock pulses.

External Device

Figure 13:
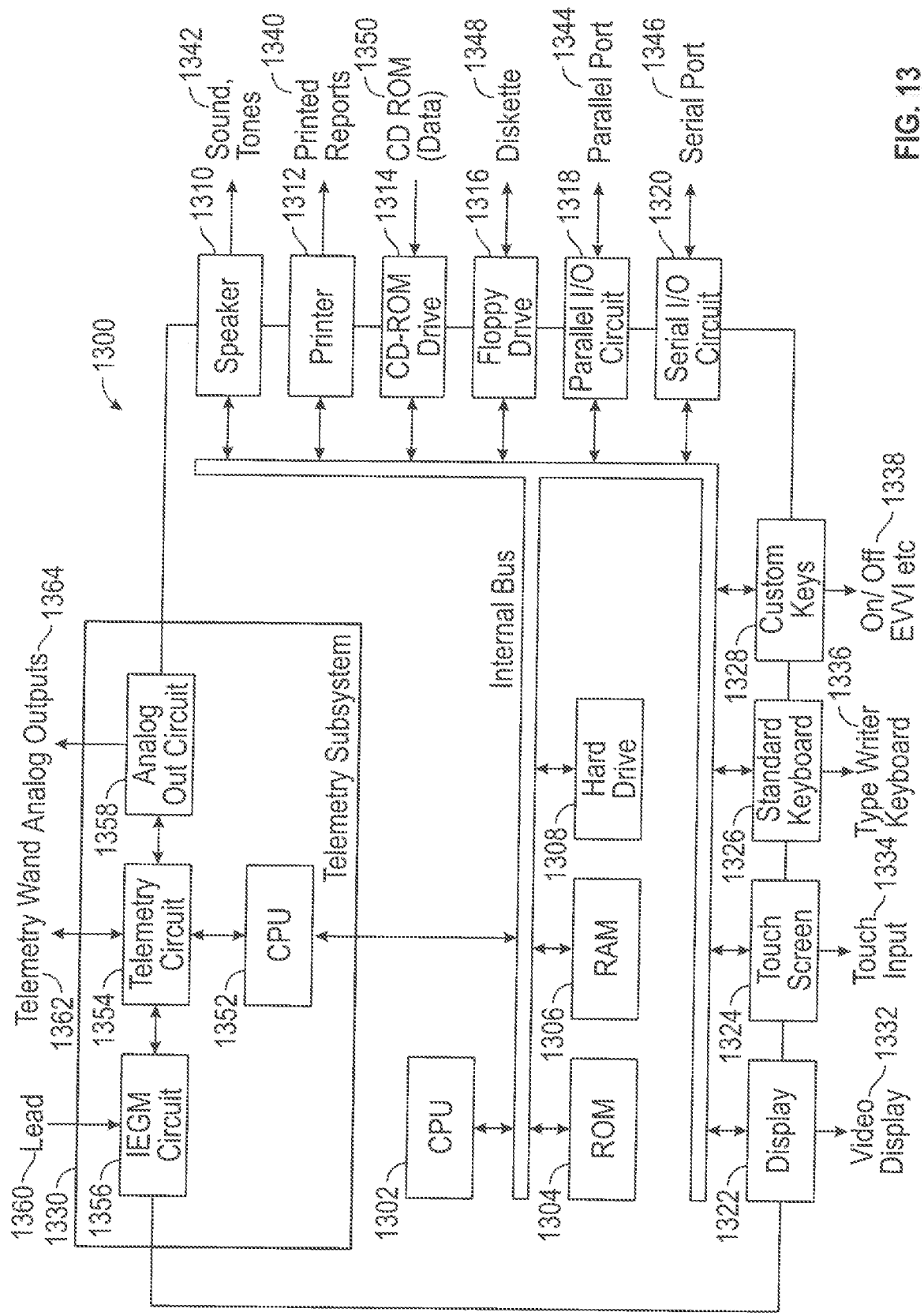
FIG. 13 illustrates a functional block diagram of the external device that is operated in accordance with embodiments herein.

FIG. 13 illustrates a functional block diagram of the external device 1300 that is operated in accordance with the processes described herein and to interface with implantable medical devices as described herein. The external device 1300 may be a workstation, a portable computer, an IMD programmer, a PDA, a cell phone and the like. The external device 1300 includes an internal bus that connects/interfaces with a Central Processing Unit (CPU) 1302, ROM 1304, RAM 1306, a hard drive 1308, the speaker 1310, a printer 1312, a CD-ROM drive 1314, a floppy drive 1316, a parallel I/O circuit 1318, a serial I/O circuit 1320, the display 1322, a touch screen 1324, a standard keyboard connection 1326, custom keys 1328, and a telemetry subsystem 1330. The internal bus is an address/data bus that transfers information between the various components described herein. The hard drive 1308 may store operational programs as well as data, such as waveform templates and detection thresholds.

The CPU 1302 typically includes a microprocessor, a micro-controller, or equivalent control circuitry, designed specifically to control interfacing with the external device 1300 and with the IMD. The CPU 1302 performs the processes discussed above. For example, the CPU 1302 may perform all or a portion of the determinations of steady state charge consumption, task related charge consumption, total charge consumption, as well as the determination of whether measured in projected cell voltages fall within tolerance ranges of one another. The CPU 1302 may perform the calibration operations described herein, as well as the various methods for determining whether early completion conditions exist and initiating warnings.

The CPU 1302 may include RAM or ROM memory, logic and timing circuitry, state machine circuitry, and I/O circuitry to interface with the IMD. The display 1322 (e.g., may be connected to the video display 1332). The touch screen 1324 may display graphic information relating to the IMD. The display 1322 displays various information related to the processes described herein. The touch screen 1324 accepts a user's touch input 1334 when selections are made. The keyboard 1326 (e.g., a typewriter keyboard 1336) allows the user to enter data to the displayed fields, as well as interface with the telemetry subsystem 1330. Furthermore, custom keys 1328 turn on/off 1338 (e.g., EVVI) the external device 1300. The printer 1312 prints copies of reports 1340 for a physician to review or to be placed in a patient file, and speaker 1310 provides an audible warning (e.g., sounds and tones 1342) to the user. The parallel I/O circuit 1318 interfaces with a parallel port 1344. The serial I/O circuit 1320 interfaces with a serial port 1346. The floppy drive 1316 accepts diskettes 1348. Optionally, the floppy drive 1316 may include a USB port or other interface capable of communicating with a USB device such as a memory stick. The CD-ROM drive 1314 accepts CD ROMs 1350.

The telemetry subsystem 1330 includes a central processing unit (CPU) 1352 in electrical communication with a telemetry circuit 1354, which communicates with both an IEGM circuit 1356 and an analog out circuit 1358. The circuit 1356 may be connected to leads 1360. The circuit 1356 is also connected to the implantable leads to receive and process IEGM cardiac signals as discussed above. Optionally, the IEGM cardiac signals sensed by the leads may be collected by the IMD and then transmitted, to the external device 1300, wirelessly to the telemetry subsystem 1330 input.

The telemetry circuit 1354 is connected to a telemetry wand 1362. The analog out circuit 1358 includes communication circuits to communicate with analog outputs 1364. The external device 1300 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 1300 to the IMD.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage elements may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method to determine an early battery depletion condition for a battery powered device, the method comprising:
   under control of one or more processors of the battery powered device, where the one or more processors are configured with specific executable instructions,
   determining a charge consumption drawn externally from a battery cell by the battery powered device for a select period of time;
   obtaining a measured cell voltage for the battery cell of the battery powered device;
   calculating a projected cell voltage based on the charge consumption; and
   declaring an early depletion condition based on a relation between the measured and projected cell voltages.

2. The method of claim 1, wherein the declaring operation comprises identifying a divergence characteristic, between the measured and projected cell voltages, that is indicative of internal battery cell self-discharge.

3. The method of claim 1, further comprising declaring a no early depletion condition when the measured and projected cell voltages fall with a tolerance range of one another.

4. The method claim 1, further comprising obtaining a steady state charge consumption and a task related charge consumption from the battery cell for the select period of time, the steady state and task related charge consumptions included within the charge consumption.

5. The method of claim 1, further comprising recalibrating at least one of the projected cell voltage or charge consumption based on the measured cell voltage when a select criteria is maintained for a predetermined period of time.

6. The method of claim 5, wherein the recalibration operation occurs when the predetermined period of time passes without a capacitor discharge task occurring.

7. The method of claim 1, wherein the calculation operation includes utilizing at least one of a i) a voltage versus capacity curve associated with the battery cell; ii) a predetermined functional relation between voltage and charge capacity, or iii) an initial cell voltage, a cell voltage rate of change and the charge consumption for the period of time.

8. The method of claim 1, wherein the estimating operation comprises obtaining an average charge consumption drained from the battery cell, and estimating the charge consumption based on the average charge consumption over a period of time.

9. The method of claim 1, further comprising, during a transient recovery interval following a capacitor discharge task, calculating a projected transient voltage and utilizing the projected transient voltage to calculate the projected cell voltage.

10. The method of claim 1, wherein the obtaining operation includes obtaining a plurality of the measured cell voltages and based thereon, determining current and past measured rates of change for cell voltages, wherein the past measured rate of change corresponds to a past period of time, the current measured rate of change corresponding to a current period of time, the declaring operation including comparing the current and past measured rates of change to determine whether a difference there between exceeds a predetermined factor.

11. The method of claim 1, wherein the charge consumption corresponds to a steady state charge consumption over the period of time, the total steady state charge consumption obtained by integrating current from steady state power usage.

12. The method of claim 1, wherein the charge consumption corresponds to task related charge consumption for one or more tasks that are tracked by the device, the task related charge consumption obtained by multiplying the corresponding average current draw during a task times the time spent performing the task, and summing the task related charge consumption for the one or more tasks.

13. The method of claim 1, wherein the determining the charge consumption is performed while the device is operating for the select period of time.

14. A system to determine an early battery depletion condition for a battery powered medical device, the system comprising:
   a processor;
   memory storing program instructions accessible by the processor;
   wherein, responsive to execution of the program instructions, the processor:
   determine a charge consumption drawn externally from a battery cell by a medical device for a select period of time;
   obtains a measured cell voltage for the battery cell of the medical device;
   calculates a projected cell voltage based on the charge consumption; and
   declares an early depletion condition based on a relation between the measured and projected cell voltages.

15. The system of claim 14, further comprising a housing for the medical device that includes the processor and memory such that the processor of the medical device declares the early depletion condition.

16. The system of claim 14, further comprising an external device to communicate with the medical device, the medical device including a measuring circuit to measure the cell voltage, the medical device including a transmitter to transmit the measured cell voltage to the external device, the external device including the memory and processor to perform the estimating, obtaining, calculating and declaring operations.

17. The system of claim 14, further comprising an external device to communicate with the medical device, the medical device and the external device including first and second processors, respectively, to share the estimating, obtaining, calculating and declaring operations.

18. The system of claim 14, wherein the processor is configured to declare a no early depletion condition when the measured and projected cell voltages fall with a tolerance range of one another.

19. The system of claim 14, wherein the processor is configured to declare recalibrate at least one of the projected cell voltage or charge consumption based on the measured cell voltage when a select criteria is maintained for a predetermined period of time.

20. The system of claim 14, wherein the calculation operation includes utilizing at least one of a i) a voltage versus capacity curve associated with the battery cell; ii) a predetermined functional relation between voltage and charge capacity, or iii) an initial cell voltage, a cell voltage rate of change and the charge consumption for the period of time.

21. The system of claim 14, wherein the estimating operation comprises obtaining an average charge consumption drained from the battery cell, and estimating the charge consumption based on the average charge consumption over a period of time.

22. The system of claim 14, wherein the processor is configured to, during a transient recovery interval following a capacitor discharge task, calculate a projected transient voltage and utilizing the projected transient voltage to calculate the projected cell voltage.

23. The system of claim 14, wherein the charge consumption corresponds to a steady state charge consumption over the period of time, the total steady state charge consumption obtained by integrating current from steady state power usage.

24. The system of claim 14, wherein the charge consumption corresponds to task related charge consumption for one or more tasks that are tracked by the device, the task related charge consumption obtained by multiplying the corresponding average current draw during a task times the time spent performing the task, and summing the task related charge consumption for the one or more tasks.

25. The system of claim 14, wherein the determining the charge consumption is performed while the device is operating for the select period of time.

26. A method to determine an early battery depletion condition for a battery powered device, the method comprising:
under control of one or more processors, where the one or more processors are configured with specific executable instructions,
obtaining a plurality of measured cell voltages;
analyzing the plurality of measured cell voltages to identify a measured rate of change;
comparing the measured rate of change with a rate of change threshold; and
declaring an early depletion condition based on a relation between the measured rate of change and the rate of change threshold.

27. The method of claim 26, further comprising determining current and past measured rates of change, wherein the past measured rate of change corresponds to a past period of time, the current measured rate of change corresponding to a current period of time, the rate of change threshold corresponding to a factor of the past measured rate of change.

28. The method of claim 26, wherein the rate of change threshold includes a set of rate of change thresholds for different conditions, the conditions including at least one of: i) light current usage condition, ii) heavy current usage condition, iii) an early in battery life condition, iv) a late in battery life condition, or v) a day to day current drain level condition.

29. The method of claim 26, wherein the measured rate of change represents a difference between two successive measured cell voltages divided by a time interval between cell voltage measurements.

30. A system to determine an early battery depletion condition for a battery powered medical device, the system comprising:
a processor;
memory storing program instructions accessible by the processor;
wherein, responsive to execution of the program instructions, the processor:
obtains a plurality of measured cell voltages;
analyzes the plurality of measured cell voltages to identify a measured rate of change;
compares the measured rate of change with a rate of change threshold; and
declares an early depletion condition based on a relation between the measured rate of change and the rate of change threshold.

31. The system of claim 30, wherein the processor is further configured to determine current and past measured rates of change, wherein the past measured rate of change corresponds to a past period of time, the current measured rate of change corresponding to a current period of time, the rate of change threshold corresponding to a factor of the past measured rate of change.

* * * * *